United States Patent
Wu

(10) Patent No.: US 9,249,154 B2
(45) Date of Patent: Feb. 2, 2016

(54) COMPOUNDS AND THERAPEUTIC USE THEREOF FOR PROTEIN KINASE INHIBITION

(71) Applicant: Zhanggui Wu, Brookline, MA (US)

(72) Inventor: Zhanggui Wu, Brookline, MA (US)

(*) Notice: Subject to any disclaimer, the term of this patent is extended or adjusted under 35 U.S.C. 154(b) by 0 days.

(21) Appl. No.: 13/668,197

(22) Filed: Nov. 2, 2012

(65) Prior Publication Data

US 2013/0143887 A1 Jun. 6, 2013

Related U.S. Application Data

(62) Division of application No. 12/349,888, filed on Jan. 7, 2008, now Pat. No. 8,318,740.

(30) Foreign Application Priority Data

Jan. 8, 2008 (CN) .......................... 2008 1 0000936

(51) Int. Cl.
*A61K 31/5025* (2006.01)
*C07D 495/04* (2006.01)

(52) U.S. Cl.
CPC .......... *C07D 495/04* (2013.01); *A61K 31/5025* (2013.01)

(58) Field of Classification Search
CPC .................................................. A61K 31/5025
USPC ........................................................ 514/248
See application file for complete search history.

(56) References Cited

PUBLICATIONS

Wikipedia, Protein kinase inhibitor, http://en.wikipedia.org/wiki/Protein_kinase_inhibitor, last modified on Dec. 2, 2013.*
Chustecka, Medscape Multispecialty, Apr. 25, 2008.*
Bo, et al., Food and Chemical Toxicology 68 (2014) 61-70.*
Stoltz, et al., Clin Cancer Res 2011;17:401-405.*
Ye, et al., Cancer Gene Therapy (2014) 21, 209-217.*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*

* cited by examiner

*Primary Examiner* — Deepak Rao
(74) *Attorney, Agent, or Firm* — Kening Li; Miller Canfield

(57) ABSTRACT

Novel compound having the following formula:

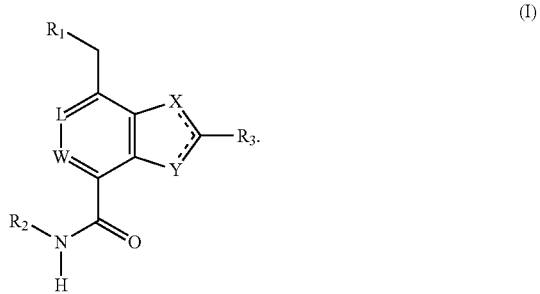

Also disclosed are a pharmaceutical compositions comprising the same, methods for treating cancer using the same, and methods for the synthesis of the same. The novel compounds of the present invention are found to inhibit protein kinases, especially Checkpoint kinase Chk1/Chk2.

17 Claims, No Drawings

COMPOUNDS AND THERAPEUTIC USE THEREOF FOR PROTEIN KINASE INHIBITION

CROSS REFERENCE TO RELATED APPLICATIONS

The present application is a divisional application of U.S. application Ser. No. 12/349,888 which claims priority to Chinese Patent application No. CN200810000936.9, filed on Jan. 8, 2008, the entire specification, drawings, and disclosure of which are incorporated herein by reference for all purposes.

FIELD OF THE INVENTION

The invention is directed to compounds, pharmaceutical compositions comprising same, and method using the same to inhibit protein kinase. The invention is further directed to methods of synthesis of the compounds and compositions.

BACKGROUND OF THE INVENTION

A major threat to human health is cancer, and worldwide at least 5 million people die from cancer annually. Most cancers in humans are caused by environmental factors. Although certain methods of cancer treatment are available, such as surgery, radiotherapy, and chemotherapy, the rate of success is still quite limited. Among available methods of treatment, chemotherapy is one of the most effective.

One category of cancer chemotherapy agents are the inhibitors or antagonists of both receptor tyrosine kinases and non-receptor tyrosine kinases. Specific targets include VEGFR, EGFR, HER2, SRC, JAK and TEK.

Certain thieno-pyridazine compounds have been found to have anti-tumor activities. For example, WO2005105808 discloses such a compound as an IKK inhibitor:

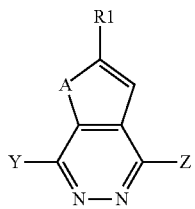

WO2007124181 discloses compounds that are inhibitors of p38 protease, a type of tyrosine kinase:

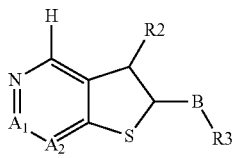

Further, WO 03029241, WO 03028731 and WO2005066163 disclose similar compounds that are inhibitors of CHK1.

Nevertheless, there is a need for more anti-cancer compounds that are inhibitors of tyrosine kinases, especially CHK1/CHK2.

DESCRIPTION OF THE INVENTION

The compounds of the present invention are anti-cancer agents that are protein kinase inhibitors, including inhibitors of Checkpoint Kinase CHK1/CHK2.

Research into checkpoints of cell cycle regulations revealed that inhibition of CHK1 expression can reverse drug resistance or tolerance of cancer cells, thereby increasing the sensitivity of cancer cells to DNA damage therapy, and dramatically increase the activities and effectiveness of anti-cancer agents. In addition, most cancers may have mutations in p53 that specifically eliminates G1/S checkpoint, which can be the basis for screening for specific anti-cancer agents.

The present invention provides novel thiophen-2-yl-pyridazine compounds or pharmaceutically acceptable derivatives thereof that have anti-cancer activities. The compounds of the present invention are inhibitors of cancer-related protein kinases such as CHK1 and CHK2, and can also increase enhance the activities of other anti-cancer agents.

This disclosure describes novel compounds and uses thereof as novel inhibitors of protein kinase, particularly checkpoint kinases as CHK1 and CHK2, which are useful for the treatment of proliferative diseases, i.e. cancer.

The novel compounds of the present invention generally have Formula I described below.

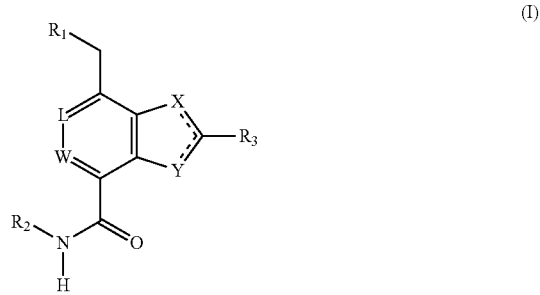

where,
X=CH; N; S, O
Y=CH; S; N, O
W=CH, N, $CR^{20}$
L=Ch, N, $CR^{20}$,
  where $R^{20}$ is selected from —$OR^{21}$; —$NR^{21}R^{22}$; —CN; —$SR^{21}$; —$S(O)R^{21}$; —$S(O)_2R^{21}$; —$S(O)_2NR^{21}R^{22}$; —$C(O)NR^{21}R^{22}$; —$N(R^{21})C(O)R^{22}$; —$N(R^{21})S(O)_2R^{22}$; —$N(R^{21})C(O)N(R^{22}R^{23})$; —$N(R^{21})C(O)OR^{22}$; heteroatom such as F, Cl, Br, I; alkyl($C_1$-$C_8$); cycloalkyl ($C_3$-$C_8$) without and with substitutions: substitutions are selected from alkyls ($C_1$-$C_8$), cycloalkyls ($C_3$-$C_8$), aryls, heteroaryls; aryl with or without substitution; heteroaryl with or without substitution; aryalkyl with or without substitution; heterocyclyl with or without substitution; heteterocyclylalkyl with or without substitution; alkenyl with or without substitution; alkynyl with or without substitution;
  wherein $R^{21}$, $R^{22}$ and $R^{23}$ is independently chosen from H, alkyl ($C_1$-$C_8$), cycloalkyls ($C_3$-$C_8$), aryl with or without substitution, alkylaryl with or without substitutions, heteroaryl with or without substitution;
$R^1$ is selected from following groups:

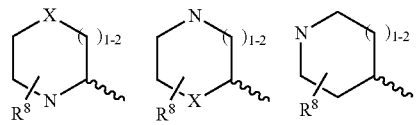

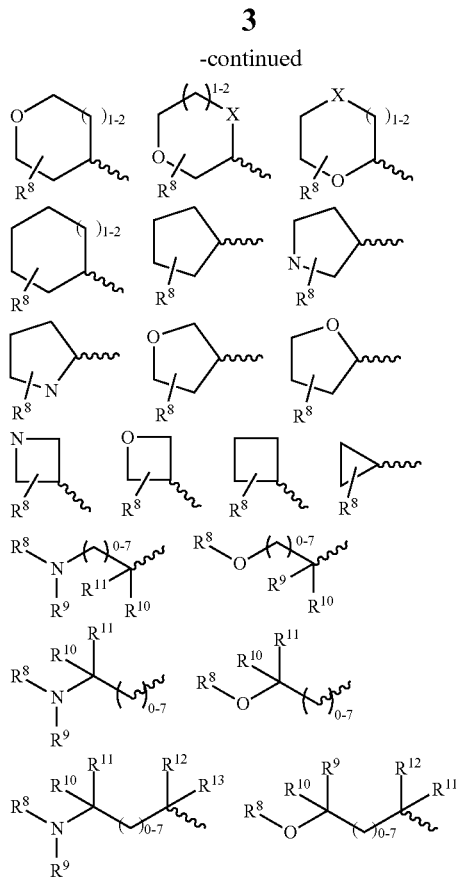

where X=CH$_2$, NH, S, or O;

R$^8$=—H, —NH$_2$, —OH, —N(R$^4$,R$^5$), —C(R$^4$R$^5$)$_{1-7}$NR$^6$R$^7$, —C(R$^4$R$^5$)$_{1-7}$OR$^6$, —N(R$^4$)NR$^5$R$^6$

R$^4$, R$^5$, R$^6$, R$^7$=H, alkyls (C$_1$-C$_6$), cycloalkyls (C$_3$-C$_8$) with or without nuclear heteroatoms such as O, S, N, aryls (selected from unsubstituted and substituted aromatics), or heteroaromatics (selected from unsubstituted and substituted heteroaromatics)

R$^9$, R$^{10}$, R$^{11}$, R$^{12}$, R$^{13}$=H, alkyls (C$^1$-C$^6$), cycloalkyls (C$^3$-C$^8$) with or without nuclear heteroatoms such as O, S, N, aryls (selected from unsubstituted and substituted aromatics) heteroaromatics (selected from unsubstituted and substituted heteroaromatics), R$^2$ is selected from a group consisting of H, OH, NH$_2$, OR$^{14}$, NR$^{14}$R$^{15}$, alkyl, aryl, heteroaryl, cycloalkyl, arylalkyl, heterocyclyl, heterocyclylalkyl, alkenyl, alkynyl, and R$^{14}$, R$^{15}$ are described as below; specifically R$^2$ is selected from the following groups:

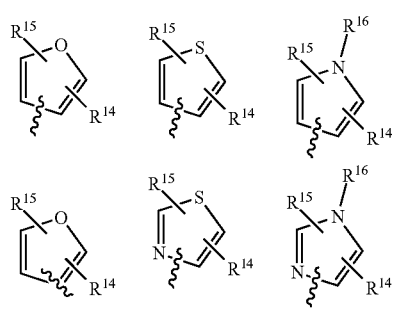

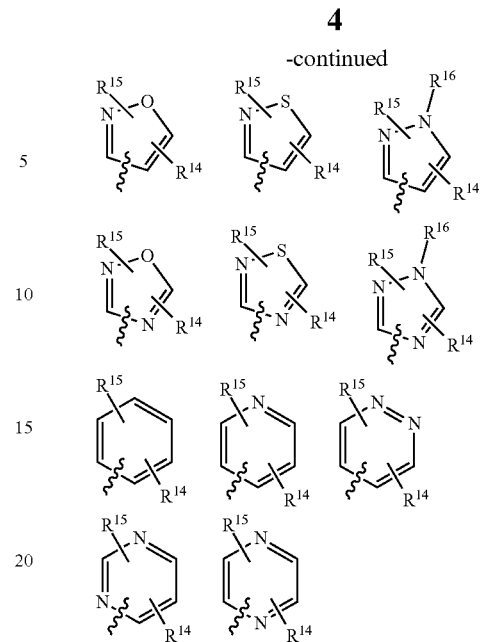

wherein R$^{14}$, R$^{15}$, R$^{16}$=H; a heteroatom such as F, Cl, Br, I; alkyl (C$_1$-C$_8$); cycloalkyl (C$_3$-C$_8$) without and with substitutions: substitutions are selected from alkyls (C$_1$-C$_8$), cycloalkyls (C$_3$-C$_8$), aryls, heteroaryls; —OR$^{17}$; —SR$^{17}$; —NR$^{17}$R$^{18}$; —S(O)R$^{17}$; —S(O)2R$^{17}$; —S(O)2NR$^{17}$R$^{18}$; —C(O)NR$^{17}$R$^{18}$; —N(R$^{17}$)C(O)R$^{18}$; —N(R$^{17}$)S(O)$_2$R$^{18}$; —N(R$^{17}$)C(O)N(R$^{18}$R$^{19}$); —N(R$^{17}$)C(O)OR$^{18}$; aryl with or without substitution; heteroaryl with or without substitution; aryalkyl with or without substitution; heterocyclyl with or without substitution; heteterocyclylalkyl with or without substitution; alkenyl with or without substitution; alkynyl with or without substitution;

where R$^{17}$, R$^{18}$ and R$^{17}$ chosen from H, alkyl (C$_1$-C$_8$), cycloalkyls (C$_3$-C$_8$), aryl with or without substitution, alkylaryl with or without substitutions, heteroaryl with or without substitution;

or, R$^{14}$, R$^{15}$ and R$^{16}$ can be part of ring which is fused containing 0-3 heteroatoms selected from N, O, and S;

R$^3$ is selected from a group consisting of H, alkyl, aryl, heteroaryl, cycloalkyl, arylalkyl, heterocyclyl, heterocyclylalkyl, alkenyl, alkynyl; preferably the following groups:

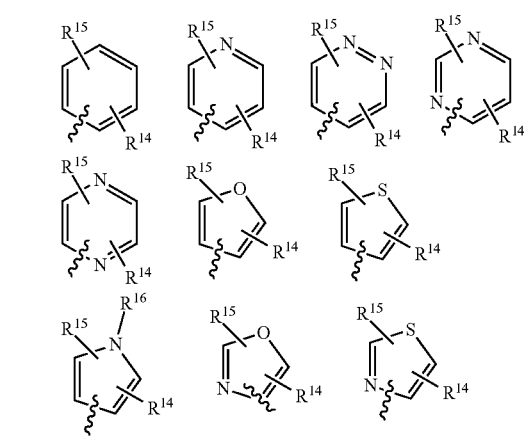

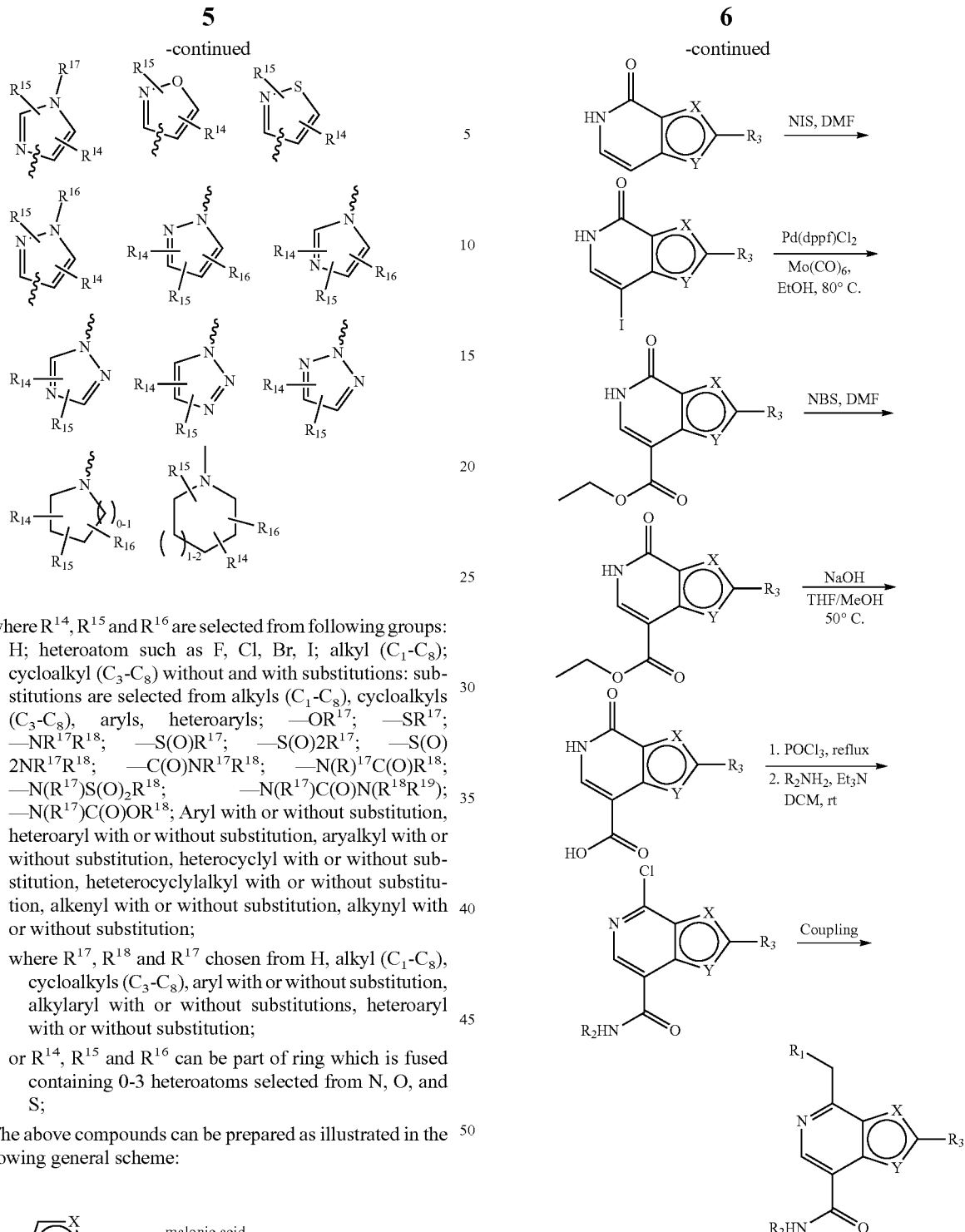

where $R^{14}$, $R^{15}$ and $R^{16}$ are selected from following groups: H; heteroatom such as F, Cl, Br, I; alkyl ($C_1$-$C_8$); cycloalkyl ($C_3$-$C_8$) without and with substitutions: substitutions are selected from alkyls ($C_1$-$C_8$), cycloalkyls ($C_3$-$C_8$), aryls, heteroaryls; —$OR^{17}$; —$SR^{17}$; —$NR^{17}R^{18}$; —$S(O)R^{17}$; —$S(O)2R^{17}$; —$S(O)2NR^{17}R^{18}$; —$C(O)NR^{17}R^{18}$; —$N(R)^{17}C(O)R^{18}$; —$N(R^{17})S(O)_2R^{18}$; —$N(R^{17})C(O)N(R^{18}R^{19})$; —$N(R^{17})C(O)OR^{18}$; Aryl with or without substitution, heteroaryl with or without substitution, aryalkyl with or without substitution, heterocyclyl with or without substitution, heterocyclylalkyl with or without substitution, alkenyl with or without substitution, alkynyl with or without substitution;

where $R^{17}$, $R^{18}$ and $R^{17}$ chosen from H, alkyl ($C_1$-$C_8$), cycloalkyls ($C_3$-$C_8$), aryl with or without substitution, alkylaryl with or without substitutions, heteroaryl with or without substitution;

or $R^{14}$, $R^{15}$ and $R^{16}$ can be part of ring which is fused containing 0-3 heteroatoms selected from N, O, and S;

The above compounds can be prepared as illustrated in the following general scheme:

The novel compounds of the present invention are inhibitors of protein kinases including CHK1 and CHK2, and can prevent DNA damage repair mechanism from arresting the cell cycle at the G2/M checkpoint. Thus these compounds have anti-proliferative (e.g. anti-cancer) activities, and can also be sued in combination with other anti-cancer agents, to enhance their anti-cancer effects. The compounds are thus useful as cancer therapeutic agents for treating humans and animals. The present invention further includes methods for making the novel compounds, pharmaceutical compositions comprising the compounds, the use of the compounds or its salts or prodrugs for the manufacture of pharmaceutical compositions, as well as methods of treatment using the pharmaceutical composition.

In a preferred embodiment, the present invention provides a compound of Formula II:

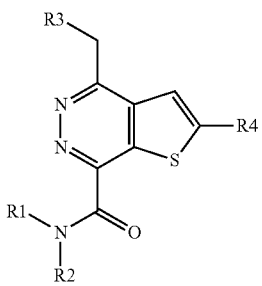
(II)

wherein $R^1$ and $R^2$ are independently H or $C_{1-4}$ alkyl;

$R^3$ is a saturated or unsaturated 5- or 6-membered ring containing at least one N, S, or O, or a stereoisomer thereof; and $R^4$ is a benezine ring substituted by one or two halogen atoms.

In one embodiment, $R^1=R^2=H$.

In a preferred embodiment, $R^3$ is a saturated 6-membered ring containing at least one N, S, or O, or a stereoisomer thereof; specifically, $R^3$ is hexahydropyridinyl, tetrahydropyranyl, tetrahydrothiopyranyl, tetrahdropyrrolidinyl, tetrahydropyrolyl, tetrahydrofuranyl, or tetrahydro-thiophenyl, or a stereoisomer thereof. Preferably, $R^3$ is hexahydropyridinyl.

Preferably, $R^4$ is a benzene ring substituted once with a halogen atom; especially,

wherein X is F, Cl, Br, or I.

Preferably, the compound of Formula II is selected from the group consisting of:

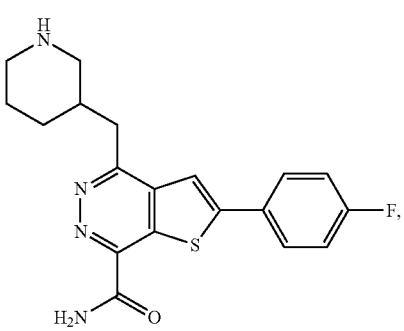
1

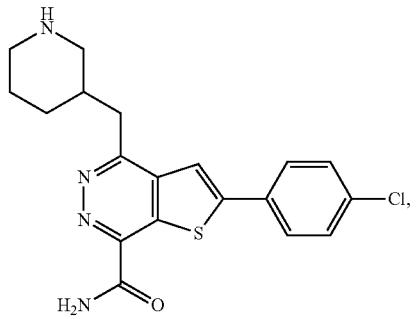
2

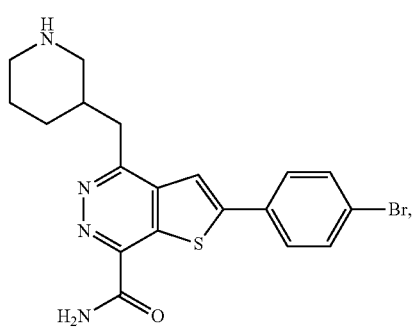
3

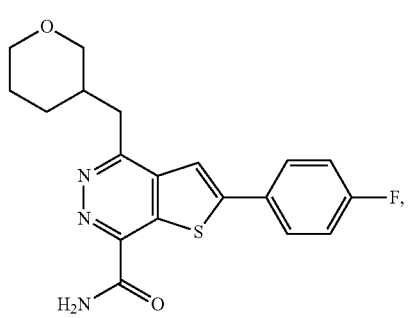
4

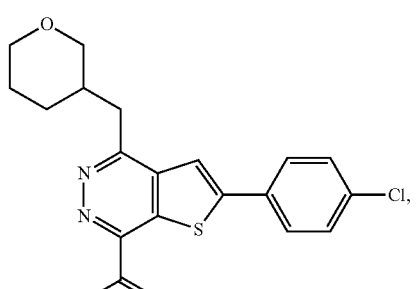
5

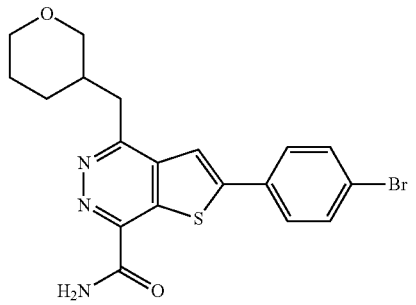
6

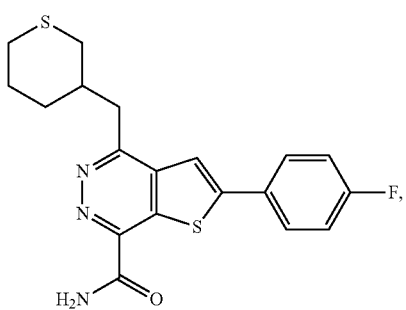
7
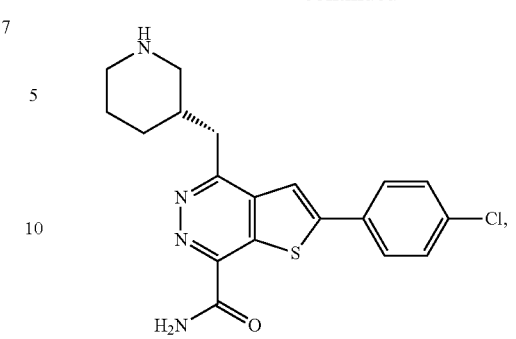
12
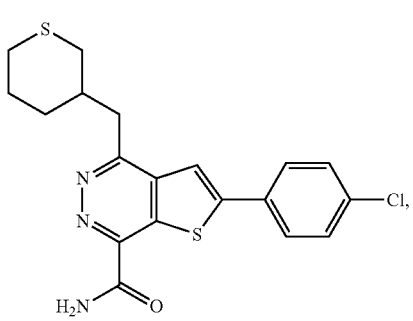
8
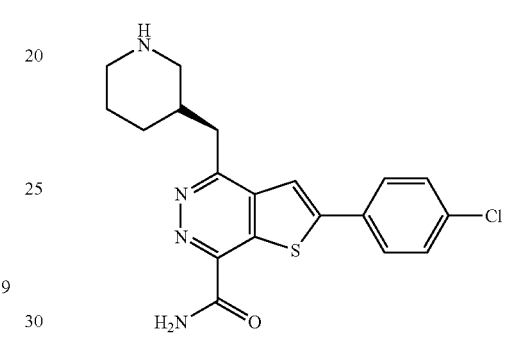
13
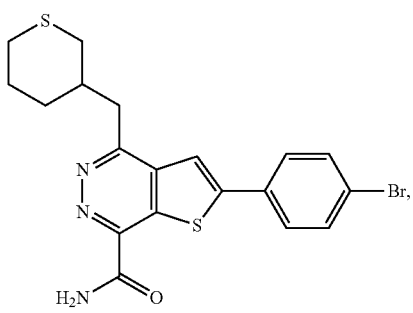
9
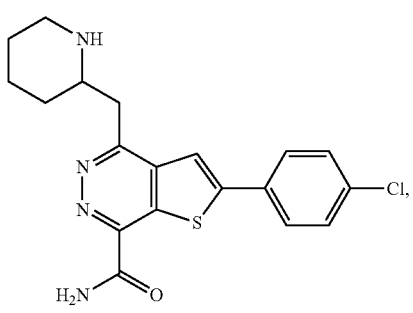
10
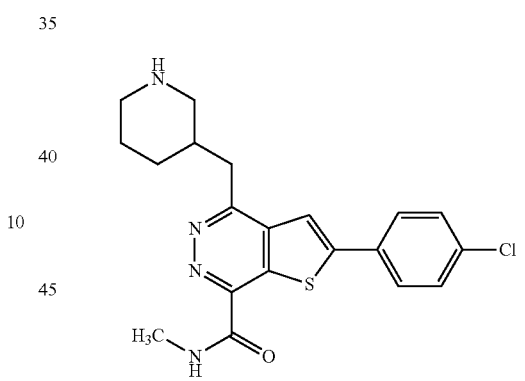
14
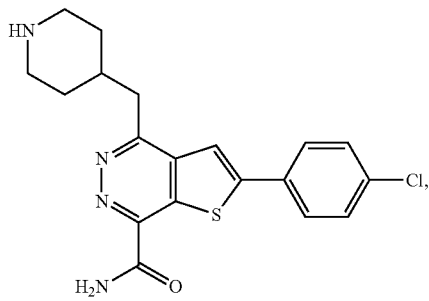
11
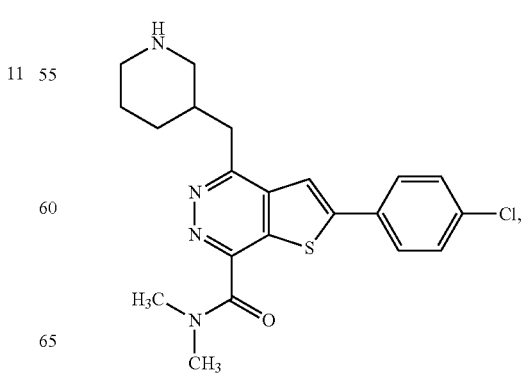
15

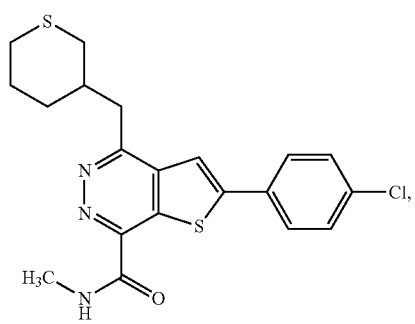
16
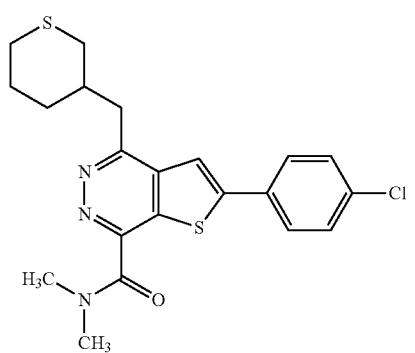
17
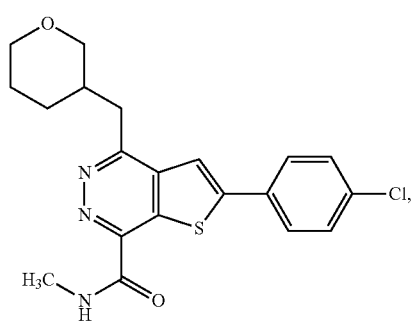
18
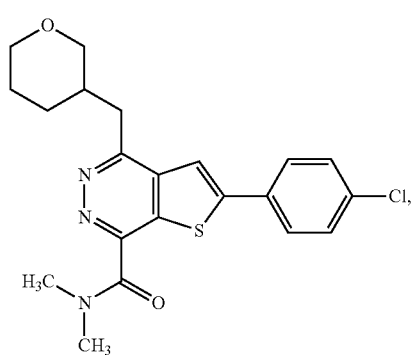
19
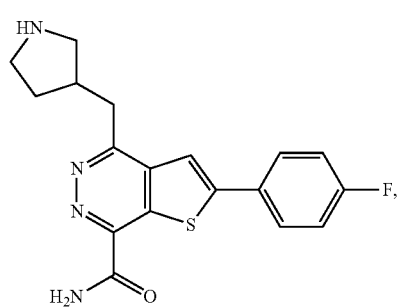
20
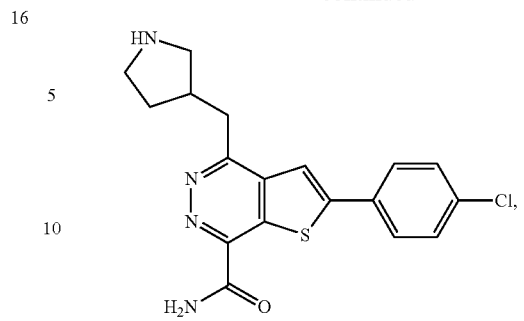
21
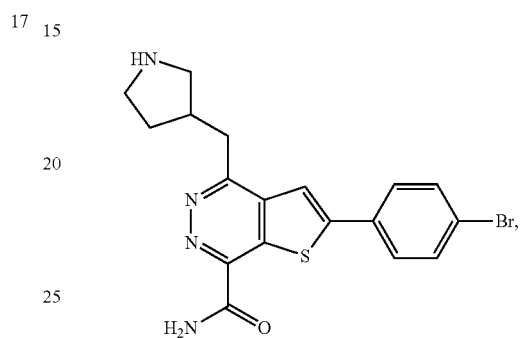
22
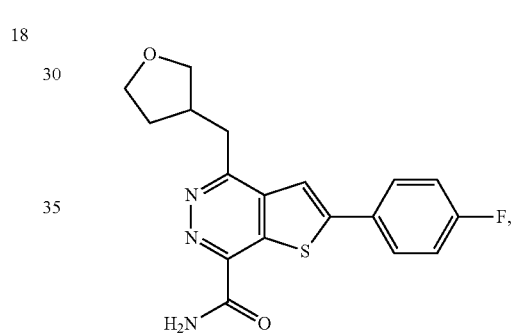
23
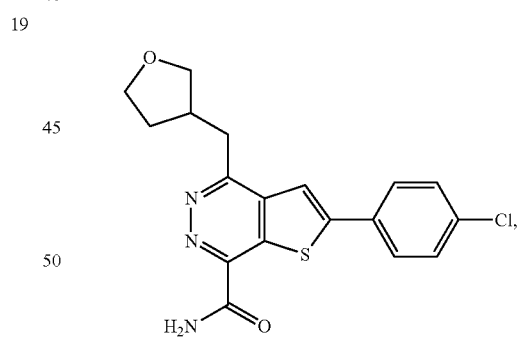
24
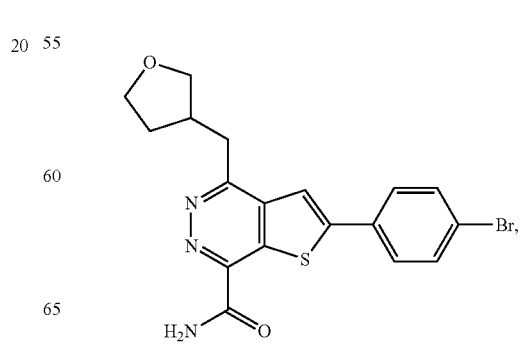
25

26
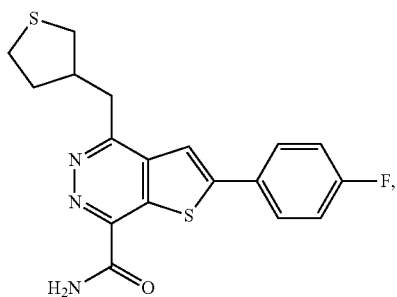
27
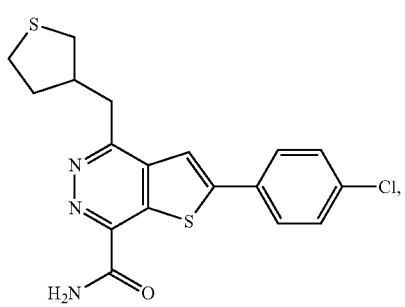
28
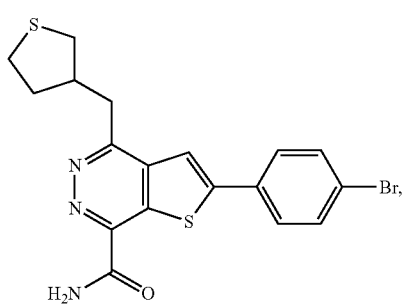
29
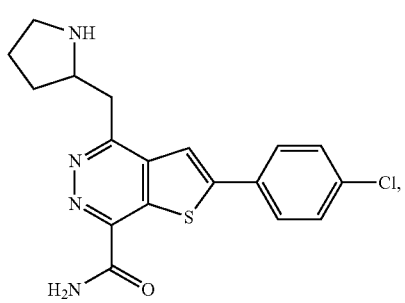
30
31
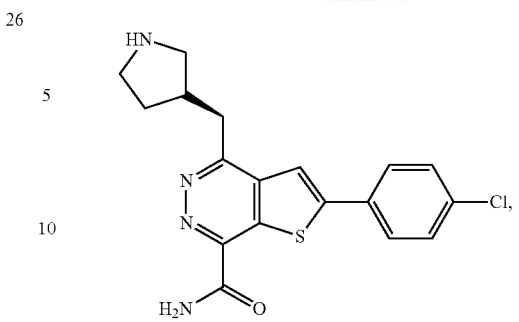
32
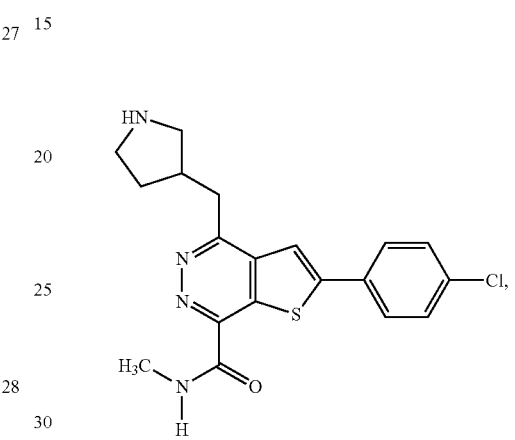
33
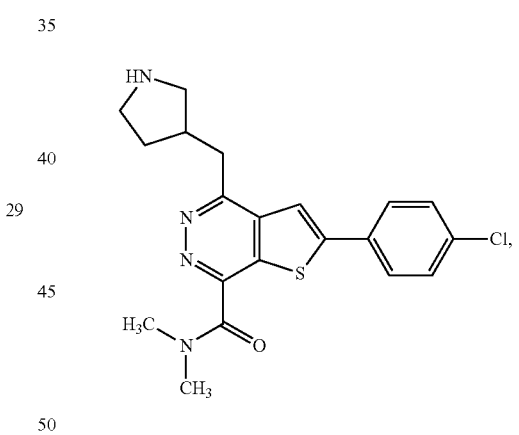
34
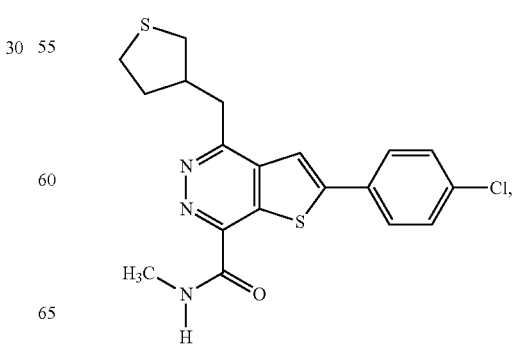

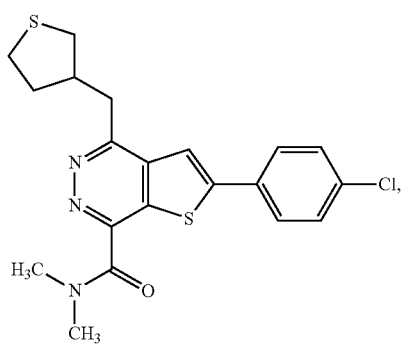
35
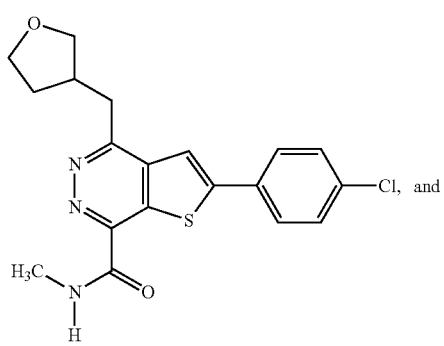
36
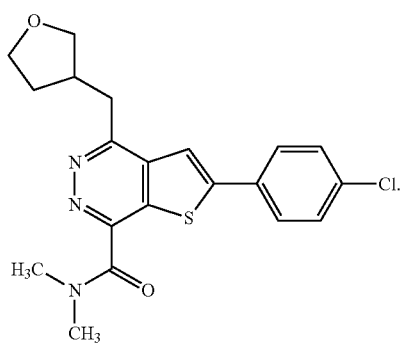
37
Preferably, R3 may also be pyridinyl, α- or γ-pyranyl, α-thiapyranyl, γ-thiapyranyl, pyrolyl, furanyl, or thiophenyl, or a stereoisomer thereof. Preferably, the compound of the invention is:
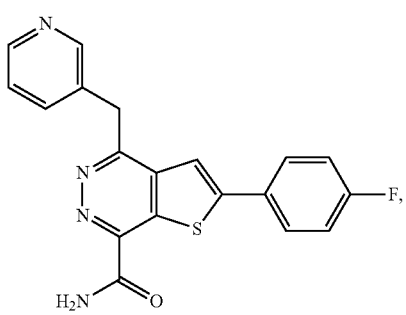
38
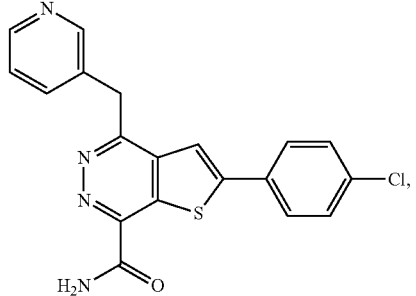
39
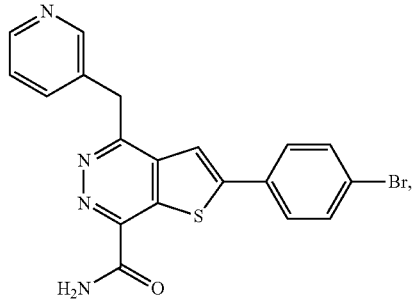
40
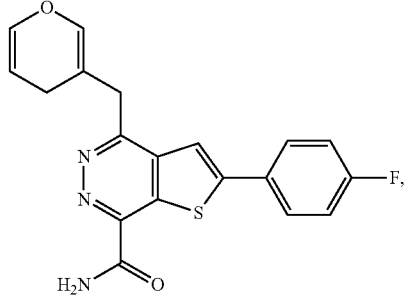
41A
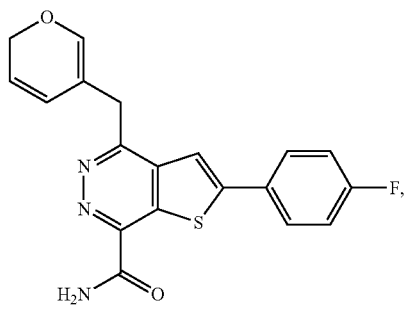
41B
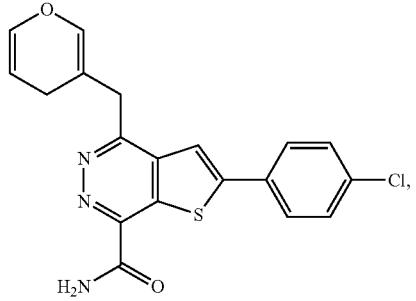
42A -continued
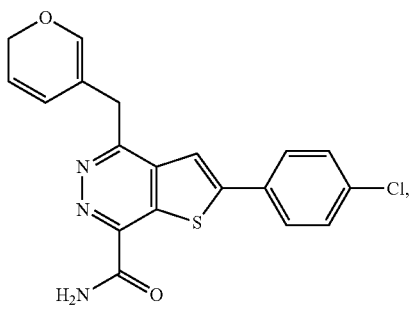 42B
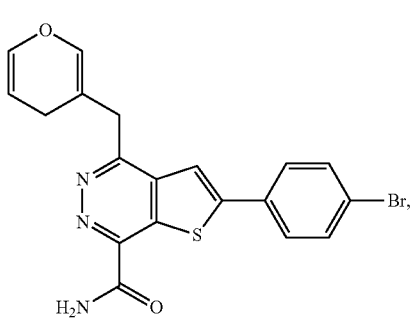 43A
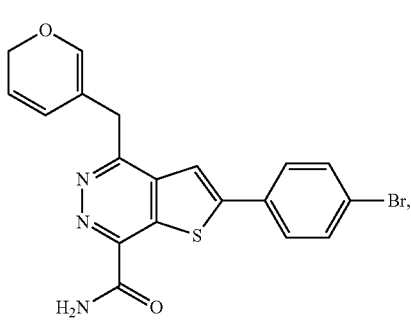 43B
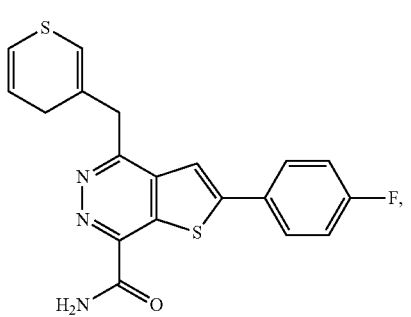 44A
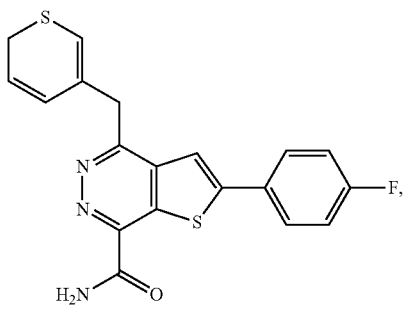 44B
-continued
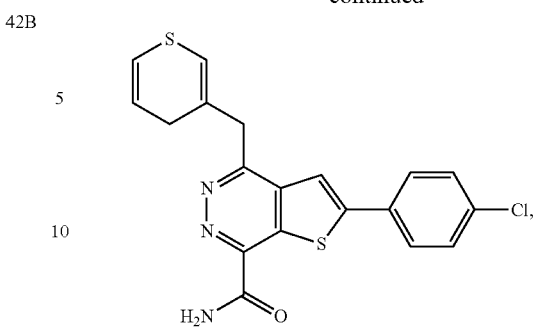 45A
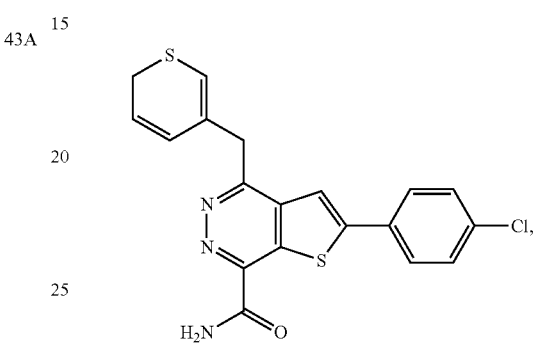 45B
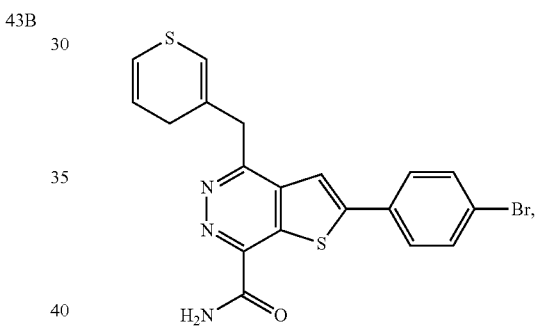 46A
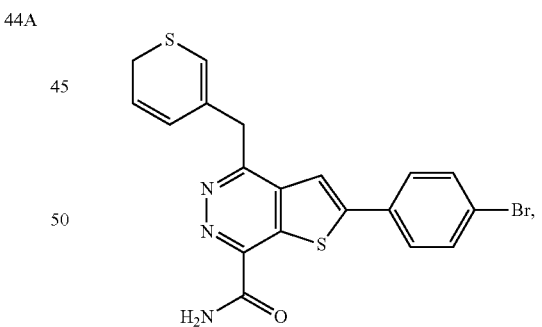 46B
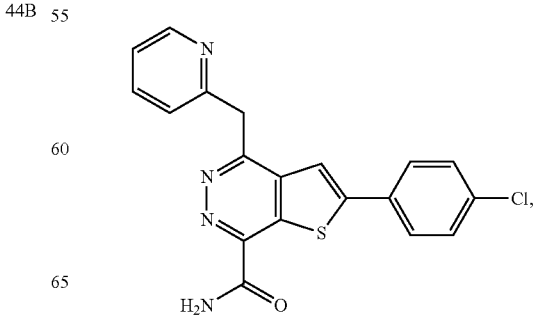 47

48
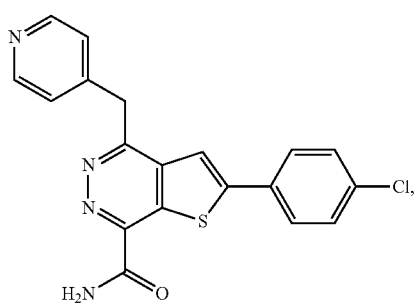
49
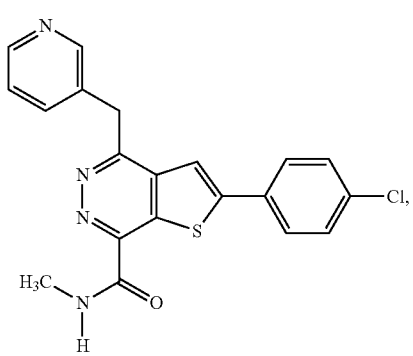
50
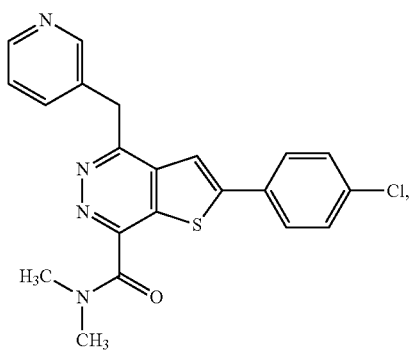
51A
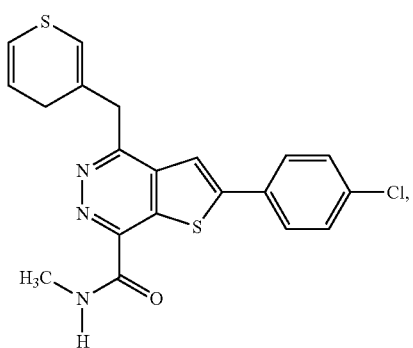
51B
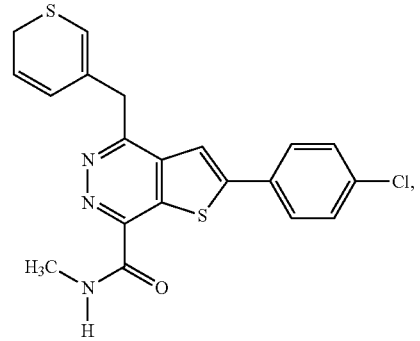
52A
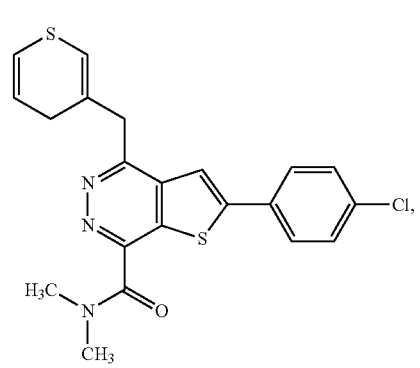
52B
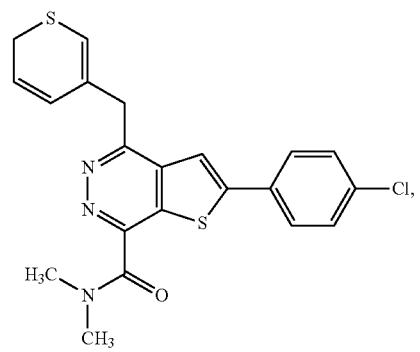
53A
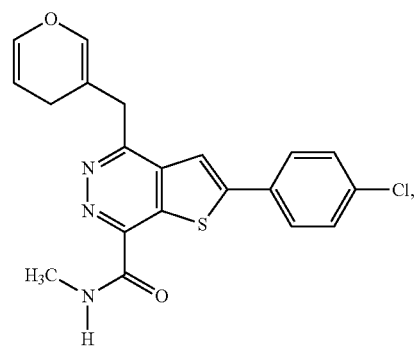

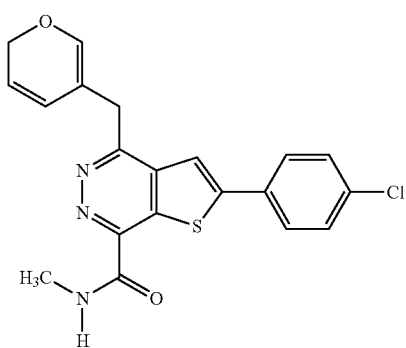
53B
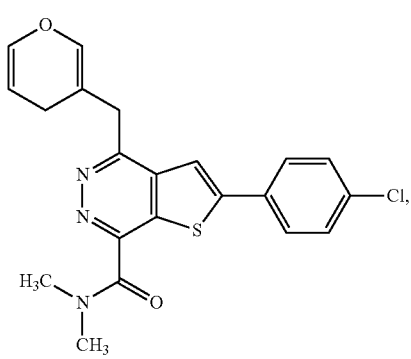
54A
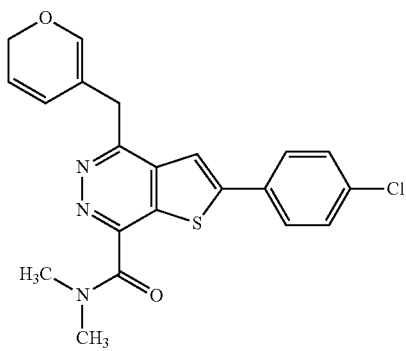
54B
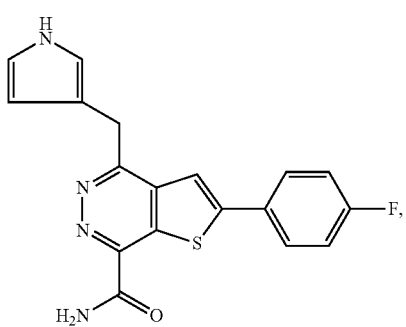
55
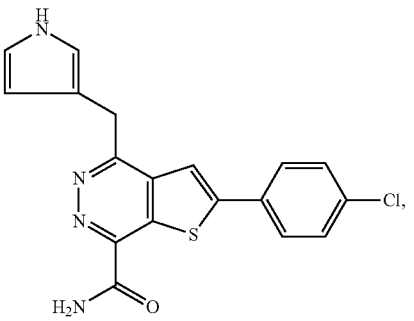
56
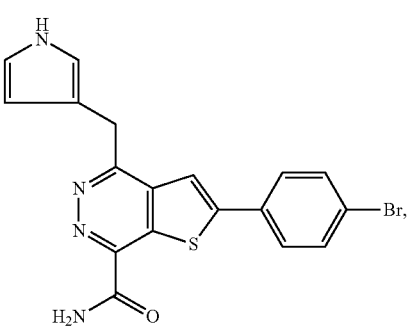
57
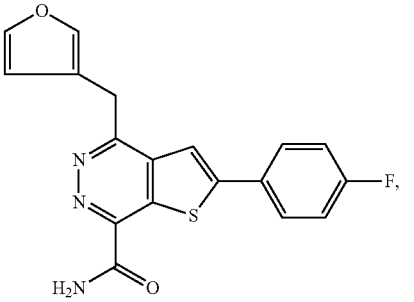
58
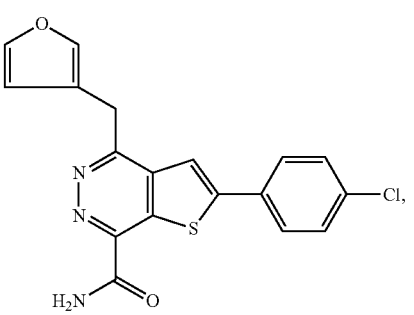
59
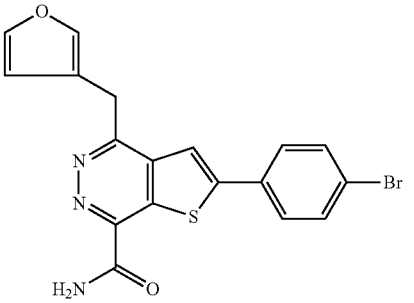
60

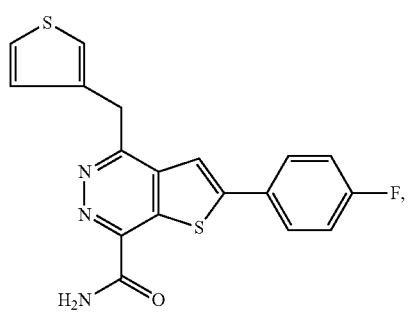
61
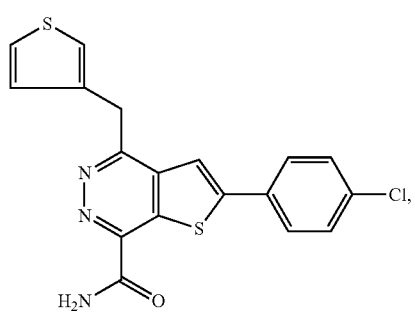
62
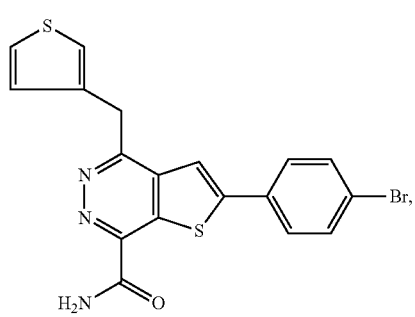
63
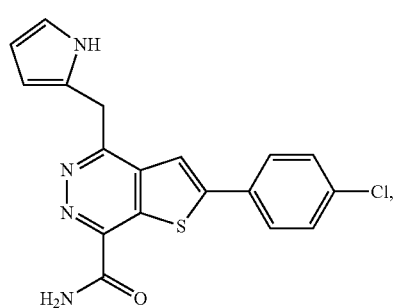
64
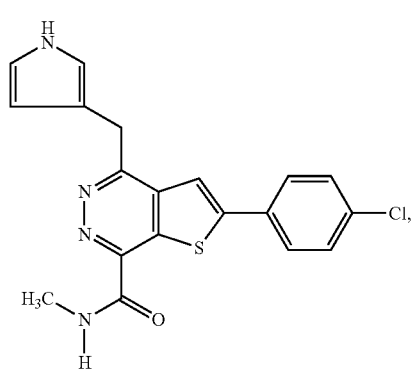
65
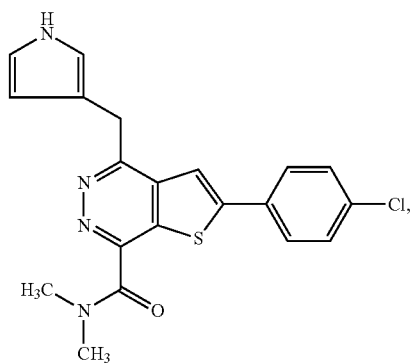
66
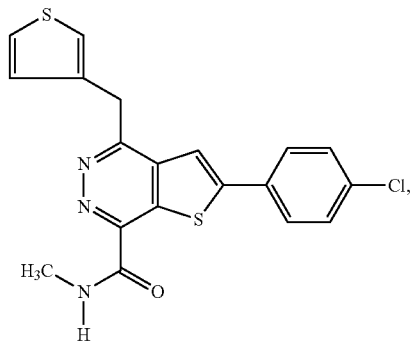
67
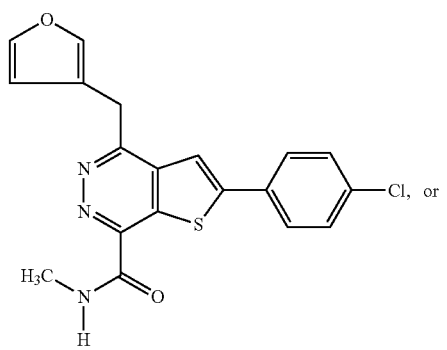
68
69

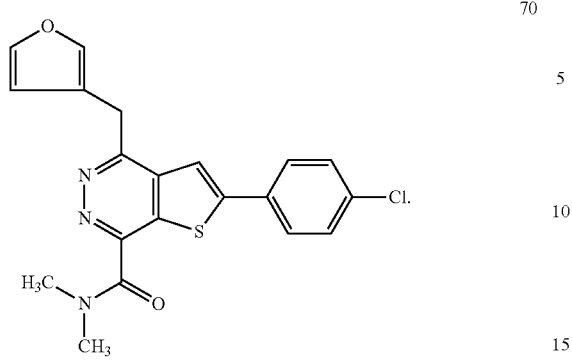
The general scheme of preparation of the compounds of the present invention is described below.
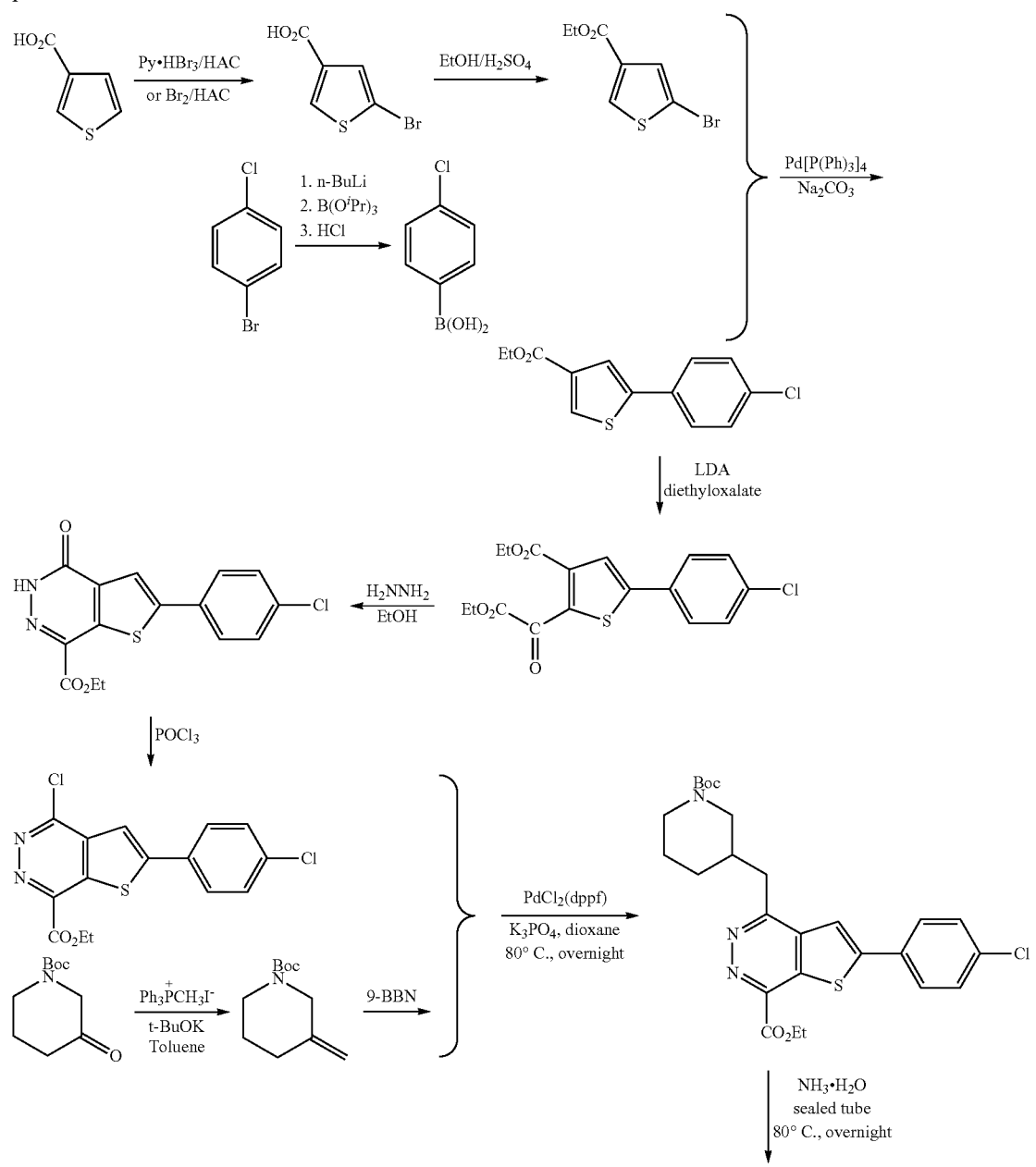

-continued

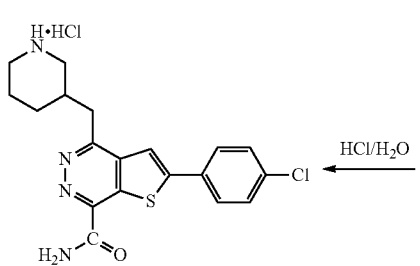 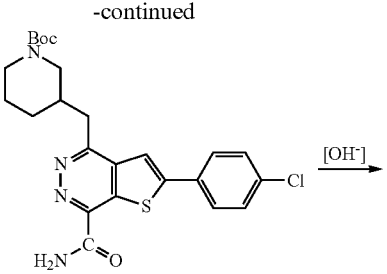 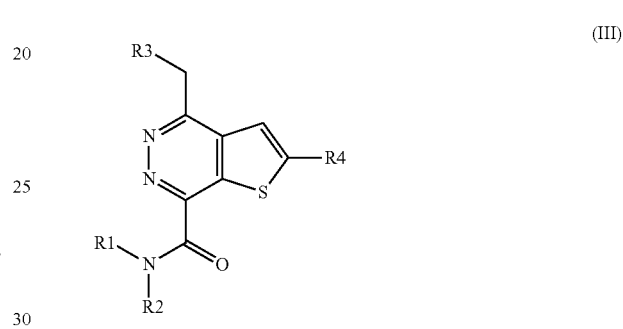

1) Under alkaline conditions, di-alkyl oxalate is used to treat a compound of Formula A:

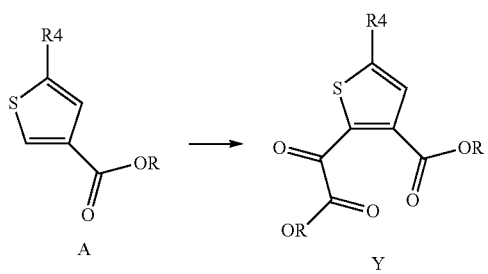

then, Y is treated with hydrazine, to produce Compound of Formula B:

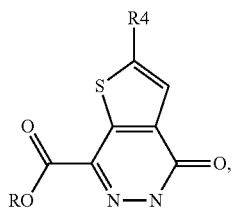

which is treated with phosphorus oxychloride, to yield Compound of Formula C:

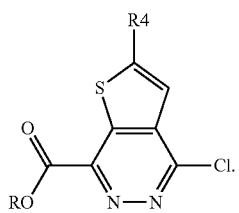

Compound of Formula C is reacted with $R^3CH_2$, yielding Compound D:

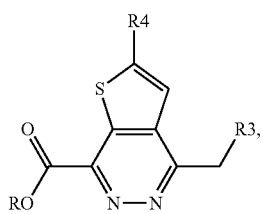

which is reacted with $NHR^1R^2$. The protective group on $R^3$ is them removed, and the compound is them treated with an alkaline, to yield the compound of Formula II, or a salt thereof:

(III)

wherein R is a $C_{1-4}$alkyl, $R^1$ and $R^2$ are independently H or $C_{1-4}$alkyl; $R^3$ is a saturated or unsaturated 5- or 6-membered ring containing N, S, or O, or a stereoisomer thereof, $R^4$ is a benzene ring substituted at any position once or twice with a halogen atom.

In the above scheme, Compound A may be obtained readily by conventional methods well-known to those skilled in the art, or purchased off-the-shelf from commercial sources. Compound A may be reacted to in the presence of a base (e.g. LDA) and a conventional organic solvent (e.g. THF) to react with oxalate dialkyl ester, such as diethyloxalate to yield compound Y. This reaction should be carried out at a low temperature due to the presence of LDA, which is prepared and used according to methods well-known to those skilled in the art.

Compound Y is reacted with hydrazine such as $_2NNH_2$ in a alcohol solvent to produce compound B, which in turn is treated with phosphorus oxychloride for a formylation reaction to produce compound C.

The above process was illustrated in part in WO2005105808 which is incorporated herein by reference.

Conventional methods may be used to prepare $R^3CH_2$ compounds with a protective group Boc. Under catalysts such as $PdCl_2$ (dppf) in solvents such as phosphate in the presence of 1,4-dioxane, with heating (about 80~90° C.), compound C may react with $R^3CH_2$ containing the protective group Boc overnight to yield compound D. It is noted that $R^3CH_2$ should be pretreated with 9-BBN (the "Suzuki-Miyaura" Reaction, see Tetrahedron Letters 45 (2004), p 6125-6128).

Compound D can be reacted with $HNR^1R^2$ under sealed condition with well-known methods, using solvents such as 1,4-dioxane, under heating (e.g. 80° C.) overnight. The protective group Boc on $R^3$ is removed under acidic conditions to obtain an acidic salt of Formula I or II, which can be treated with a base to obtain a compound of Formula I or II.

Compounds of the present invention have been found to be inhibitors of protein kinases, including both receptor tyrosine kinases and non-receptor tyrosine kinases, especially Checkpoint Kinase CHK1 and CHK2.

In another embodiment, the present invention provides a pharmaceutical composition comprising a compound described above and a pharmaceutically acceptable adjuvant or excipient, and a method for treating cancer by administering an effective amount of the pharmaceutical composition to a patient in need thereof. Administration of an "effective amount" or a "therapeutically effective amount" of a compound of the present invention means an amount that is useful, at dosages and for periods of time necessary to achieve the desired result. The therapeutically effective amount of a compound in accordance with the present invention may vary according to factors, such as the disease state, age, sex, and weight of the subject. Dosage regimens in the patient may be adjusted to provide the optimum therapeutic response. For example, several divided doses may be administered daily or the dose may be proportionally reduced as indicated by the exigencies of the therapeutic situation. In the context of the present invention, a "pharmaceutically acceptable salt," refer to salts prepared from pharmaceutically acceptable, non-toxic acids.

The pharmaceutical compositions according to the invention can be present and administered as liquid, semi-solid or solid medicament forms and in the form of e.g. injection solutions, drops, juices, syrups, suspensions, sprays, granules, tablets, pellets, patches, capsules, plasters, suppositories, ointments, creams, lotions, gels, emulsions or aerosols, and comprise a compound of the present invention, and pharmaceutical auxiliary substances according to the galenical form, such as e.g. carrier materials, fillers, solvents, diluents, surface-active substances, dyestuffs, preservatives, disintegrating agents, anti-friction agents, lubricants, flavorings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, ground nut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crosspovidone, agar and bentonite. The choice of auxiliary materials and the amounts thereof to be employed depend on whether the medicament is to be administered orally, perorally, subcutaneously, parenterally, intravenously, intraperitoneally, intradermally, intramuscularly, intranasally, buccally, rectally or locally, for example to infections on the skin, the mucous membranes and the eyes. Formulations in the form of tablets, coated tablets, capsules, granules, drops, juices and syrups are suitable, inter alia, for oral administration, and solutions, suspensions, easily reconstitutable dry formulations and sprays are suitable for parenteral, topical and inhalatory administration. A compound according to the invention in a depot in dissolved form or in a patch, optionally with the addition of agents which promote penetration through the skin, are suitable formulations for percutaneous administration. Formulation forms which can be used orally or percutaneously can release the compound according to the invention in a delayed or controlled manner.

The medicaments and pharmaceutical compositions according to the invention are prepared with the aid of agents, devices, methods and processes which are well-known in the prior art of pharmaceutical formulation, such as are described, for example, in Remington's Pharmaceutical Sciences, 18th ed., Mack Publishing Co., Easton, Pa. (1990), in particular in part 8, sections 76 to 93.

Thus for a solid formulation, such as a tablet, the active compound of the medicament, can be mixed with a pharmaceutical carrier, e.g. conventional tablet constituents, such as maize starch, lactose, sucrose, sorbitol, talc, magnesium stearate, dicalcium phosphate or gum, and pharmaceutical diluents, such as e.g. water, in order to form a solid preformulation composition which comprises a compound according to the invention or a pharmaceutically acceptable salt thereof in homogeneous distribution. Homogeneous distribution here is understood as meaning that the active compound is distributed uniformly over the entire preformulation composition, so that this can easily be divided into unit dose forms of the same action, such as tablets, pills or capsules. The solid preformulation composition is then divided into unit dose forms. The tablets or pills of the medicament according to the invention or of the compositions according to the invention can also be coated, or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

The amount of active compound to be administered to the patient varies and depends on the weight, age and disease history of the patient, as well as on the mode of administration, the indication and the severity of the disease. A range of does, for example 0.1 to 5,000 mg/kg, in particular 1 to 500 mg/kg, preferably 2 to 250 mg/kg of body weight of a compound according to the invention are usually administered.

The pharmaceutical composition of the present invention may be administered enterally (such as orally or via rectal administration), externally, or parenterally e.g. via injection. Suitable formulations include tablets (such as conventional tablets, buccal tablets, sublingual tablet, oral cavity patch, chewable tablet, effervescent tablet, vaginal tablet, vaginal effervescent tablet, sustained-release tablet, controlled release tablet, enteric coated tablet, buccal rapid-release tablet), capsules (hard capsules, soft capsules, sustained-release capsules, controlled-release capsules, enteric-coated capsules, etc), pills (dripping pills, sugar coated pills, pellets), oral liquid (oral solution, oral suspension, oral emulsion, etc), granules (suspension granules, soluble granules, effervescent granules, gastro-resistant granules, sustained-release granules, controlled-release granules, etc), injection (injectable solution, injectable emulsion, injectable suspension), intravenous infusion, powder for injection, concentrated solution for injection, implants, etc, and other medicament form such as suppositories, aerosol, aerosol powder, spray, gel, pellicles, patches, etc.

Compounds of the present invention may be incorporated into biodegradable polymers allowing for sustained release of the compound, the polymers being implanted in the vicinity of where drug delivery is desired, for example, at the site of a tumor or implanted so that the compound is slowly released. The biodegradable polymers and their use are described, for example, in detail in Brem et al., J. Neurosurg. 74:441-446 (1991). Osmotic mini pumps may also be used to provide controlled delivery.

Toxicity and therapeutic efficacy of such compounds can be determined by standard pharmaceutical procedures in cell cultures or experimental animals, e.g., for determining the LD50 (the dose lethal to 50% of the population) and the ED50 (the dose the therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

Pharmaceutical composition of the present invention is suitable for treating cancers and the related diseases, and may be used alone or in combination with other anti-cancer drugs. An ordinarily skilled person in the art will be able to determine the suitable dosage for the treatment, depending on the types of disease to be treated, the formulation and the conditions of the patient.

The compounds of this invention can be used to prevent or treat abnormal cell proliferation, especially those found in tumors or cancers, including lung cancer, liver cancer, leucocythaemia, osteocarcinoma, pancreas cancer, skin cancer, melanoma, metrocarcinoma, oophoroma, rectal carcinoma, gastric carcinoma, colon cancer, breast carcinoma, salpinx carcinoma, endometrium carcinoma, cervix carcinoma, vagina carcinoma, carcinoma of vulva, esophagus carcinoma, small intestine carcinoma, incretion carcinoma, soft tissue sarcoma, urethra carcinoma, prostatic cancer, lymphocytoma, bladder cancer, nephridium cancer, tumors of vertebral column, tumors in the neuroglia of the brain, and pituitary adenoma.

The pharmaceutical composition of the present inveniton may also be used for the prevention or treatment of autoimmune diseases, inflammation, nerve system diseases, and cardiovascular diseases. Especially, the pharmaceutical compositions of the present invention may be used to treat cell cycle-related or cell proliferation related diseases.

EXAMPLES

Example 1

Synthesis of 2-(4-chlorophenyl)-4-(3-piperidinemethyl)-thieno[2,3-d]pyridazine-7-carboxylic acid amide Step 1: 5-bromo-thiophene-3-carboxylic acid

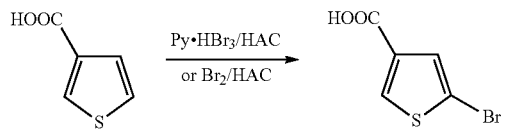 [SMILES: O=C(O)c1ccsc1 ; O=C(O)c1csc(Br)c1]

To a solution of thiophene-3-carboxylic acid (12.6 g, 0.1 mol) in AcOH (96 ml), being stirred at room temperature, HBr solution (8 ml) was added, and the stirring continued until the color of mixture turned to yellow. Pyridinium bromide perbromide (27 g) was then sequentially added. The mixture was poured into ice-water, stirred for about 30 minutes. A white precipitate was formed, which was filtered and dried to obtain 5-bromo-thiophene-3-carboxylic acid (10.8 g) as a white solid after crystallization in hot water. HPLC: 92%.

Step 2: 5-bromo-thiophene-3-carboxylicacid ethyl ester

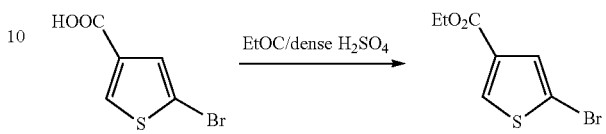

5-bromo-thiophene-3-carboxylic acid (18.2 g, 0.09 mol) was dissolved in absolute ethanol (150 ml) and $H_2SO_4$ (5 ml), and the mixture was refluxed for 5 hours. The mixture was concentrated under vacuum to give a yellow oil, then diluted with a mixture of ethyl acetate (100 ml) and saturated brine (200 ml), and mixed, let standing for layer separation. The aqueous layer was washed with ethyl acetate (25 ml twice). The extract and the organic layer was adjusted with $Na_2CO_3$ (10%) to pH=8, and the organic phase was separated and washed with saturated brine to pH=7, dried over anhydrous $Na_2SO_4$ over night. The organic layer was concentrated under reduced pressure to give 5-bromo-thiophene-3-carboxylic acid ethyl ester as yellow oil (15 g).

Step 3: 4-chlorophenylboric acid

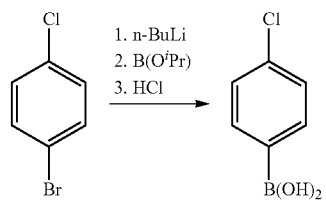 [SMILES: Clc1ccc(Br)cc1 ; OB(O)c1ccc(Cl)cc1]

A solution of 4-chloro-bromophenyl (70.6 g) was dissolved in a mixture of toluene (588.3 ml) and THF (147 ml) under argon, and n-BuLi (176.4 ml, 2.5M in hexane) was added dropwise at −78° C., stirred for 1 hours, then tri-isopropyl borate (109.2 ml) was added dropwise at −78° C., stirred for 1 hour. HCl (360.4 ml, 2.2 mol/l) was added at −20° C., and warmed to 10° C., the reaction was diluted with water, the aqueous layer was extracted with toluene (35 ml, twice). The extract and the organic layer were washed with saturated brine, dried over anhydrous $Na_2SO_4$ over night. The organic layer was concentrated under reduced pressure to give 4-chlorophenylboric acid (48 g) as a solid after crystallization (toluene).

Step 4: 5-(4-chlorophenyl)-3-thiophenecarboxylic acid ethyl ester

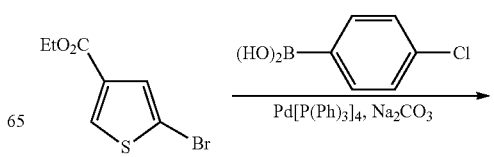

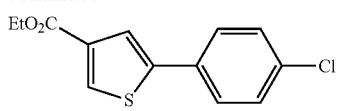

5-(4-chlorophenyl)-3-thiophenecarboxylic acid ethyl ester (10.5 g), 4-Chlorophenylboronic acid (6 g), Na₂CO₃ (7.5 g), Pd[P(Ph)3]4 (1.5 g) and a solvent mixture of toluene:H₂O:EtOH (4:2:1 v/v) were mixed and heated at reflux for 3 hours. The progress of the reaction was followed by TLC. The resulting reaction mixture was cooled to room temperature, diluted with toluene and washed with saturated brine, the aqueous layer was extracted with toluene (35 ml, 2×). The extract and the organic layer was washed with saturated brine, dried over anhydrous Na₂SO₄ over night. The organic layer was concentrated under reduced pressure to 5-(4-chlorophenyl)-3-thiophenecarboxylic acid ethyl ester (8.6 g) as a solid after crystallization in absolute EtOH.

1HNMR (500 MHz, DMSO), δ 8.30 (s, 1H), 7.81 (s, 1H), 7.72 (m, 2H), 7.46 (m, 2H), 4.27 (m, 2H), 1.30 (m, 3H)

Step 5: 5-(4-chlorophenyl)-2-thiophene-3-carboxylic acid ethyl ester

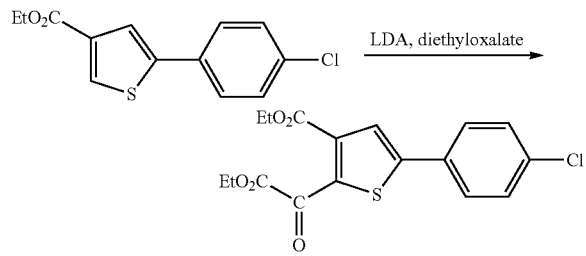

A mixture of 5-(4-chlorophenyl)-3-thiophenecarboxylic acid ethyl ester (28.7 g) and diethyloxalate (29.7 ml) in dried THF (1084 ml) was cooled in dry-ice acetone bath and a solution of LDA in THF was added drop-wise. The reaction mixture was stirred for 10 min at ice bath temperature and then quenched with diluted HCl at room temperature. The reaction was diluted with water, washed with saturated brine, and dried over anhydrous Na₂SO₄. The residue obtained after evaporation was recrystallized by EtOH to obtain 5-(4-chlorophenyl)-2-thiophene-3-carboxylic acid ethyl ester (25.5 g).

1HNMR (500 MHz, CD3Cl), δ 7.61 (s, 1H), 7.59 (m, 2H), 7.42 (m, 2H), 4.37 (m, 4H), 1.39 (m, 6H).

Step 6: 2-(4-chlorophenyl)-4-oxo-4,5-dihydro-thiero[2,3-d]pyridazine-7-carboxyllic acid ethyl ester To a solution of 5-(4-chlorophenyl)-2-thiophene-3-carboxylic acid ethyl ester in ethanol (45 ml) was added hydrazine hydrate (0.75 ml). The mixture was heated at 70° C. for 1 hours, and cooled to room temperature. The solid of 2-(4-chlorophenyl)-4-oxo-4,5-dihydro-thiero[2,3-d]pyridazine-7-carboxyllic acid ethyl ester (2.75 g) was collected by filtration, washed with a mixture of dichloromethane/hexane (1:1) and dried.

Step 7: 4-chloro-2-(4-chlorophenyl)-thieno[2,3-d]pyridzaine-7-carboxylic acid ethyl ester

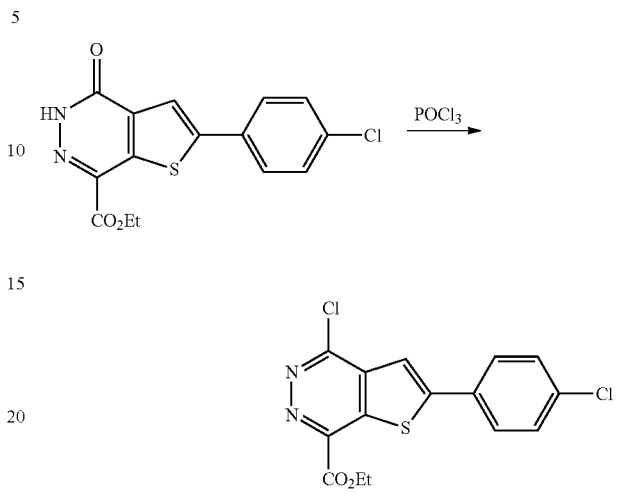

A mixture of 2-(4-chlorophenyl)-4-oxo-4,5-dihydro-thiero[2,3-d]pyridazine-7-carboxyllic acid ethyl ester (1.5 g) in phosphorous oxychloride (22.5 ml) was heated at 90° C. for 3 h, cooled to room temperature and evaporated under reduced pressure to dryness. To the residue was added ice and ethyl acetate and the pH was adjusted with potassium carbonate solid. The organic layer was separated, washed with water, brine, and dried over anhydrous Na₂SO₄. The organic layer was evaporated to dryness to obtain 4-chloro-2-(4-chlorophenyl)-thieno[2,3-d]pyridzaine-7-carboxylic acid ethyl ester (1.0 g).

1HNMR (500 MHz, CD3Cl), δ 7.74 (m, 3H), 7.59 (m, 2H), 4.65 (m, 2H), 1.55 (m, 3H). HRMS (high resolution MS) MW=351.98.

Step 8: N-Boc-3-methylenepiperidine

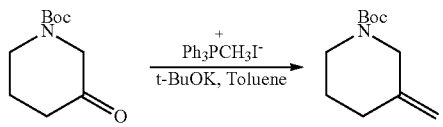

To a mixture of triphenylmethylphosphonium iodide (22.14 g) in toluene (135 ml) was added potassium tert-butanolate (5.32 g). The solution turned to orange. Then N-Boc-3-piperidone (6.0 g) in toluene (66 ml) was dropped into the solution under argon, at 30° C. The reaction was filtered and washed with water (200 ml, 2×) and then diluted by HCl (1M), dried with anhydrous sodium sulfate. The solution was purified by flash chromatography (silica gel, PE:EA=15:1) to obtain N-Boc-3-methylenepiperidine as an oil (4.2 g).

1HNMR (400 MHz, CD3Cl), δ 4.83 (s, 1H), 4.76 (s, 1H), 3.89 (s, 2H), 3.45 (m, 2H), 2.26 (m, 2H) 1.64 (s, 2H), 1.51 (s, 9H).

Step 9: 4-(1-Boc-3-piperidinemethy)-2-(4-chlorophenyl)-thieno[2,3-d]pyridazine-7-carboxylic acid ethyl ester

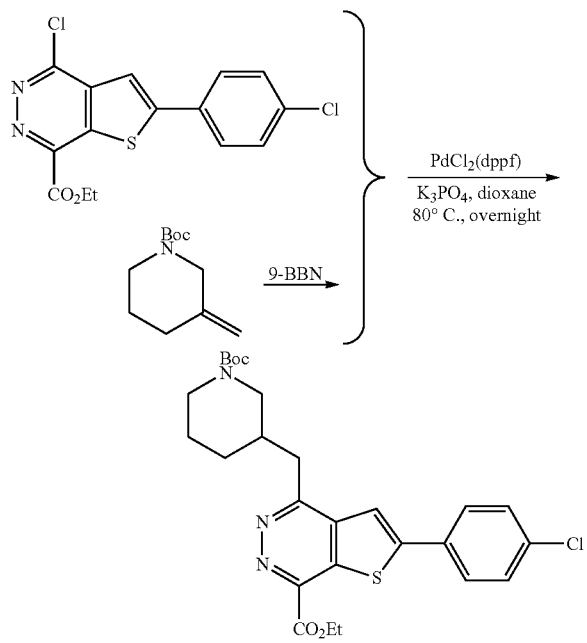

A mixture of N-Boc-3-methylenepyrazdine (0.4 g) and 9-BBN (12 ml) was cooled to 0° C. for 30 min, and then warmed to room temperature for 2 h. Dioxane (20 ml), PdCl$_2$ (0.05 g), K$_3$PO$_4$ (0.32 g) and 4-chloro-2-(4-chlorophenyl)-thieno[2,3-d]pyridzaine-7-carboxylic acid ethyl ester were heated at 90° C. over night. The reaction mixture was cooled, diluted with ethyl acetate and washed with water. The organic layer was washed with brine, dried over anhydrous Na$_2$SO$_4$ and evaporated. The residue was purified by flash chromatography (silica gel, PE:EA=5:10) to obtain 4-(1-Boc-3-piperidinemethy)-2-(4-chlorophenyl)-thieno[2,3-d]pyridazine-7-carboxylic acid ethyl ester as a solid (0.3 g).

1HNMR (400 MHz, DMSO), δ 8.90 (s, 1H), 8.03 (m, 2H), 7.63 (m, 2H), 4.54 (m, 2H), 3.73 (s, 2H), 3.32 (m, 2H), 3.28 (m, 1H), 2.82 (m, 2H), 2.09 (s, 1H), 1.78 (s, 1H), 1.64 (s, 1H), 1.44 (m, 3H), 1.39 (s, 1H), 1.32 (s, 9H).

MS (EI):515 (M+), 486, 458, 442, 414, 334, 332, 306, 304, 149, 57.

Step 10: 4-(1-Boc-3-piperidinemethy)-2(4-chlorophenyl)-thieno[2,3-d]pyridazine-7-carboxylic acid amide

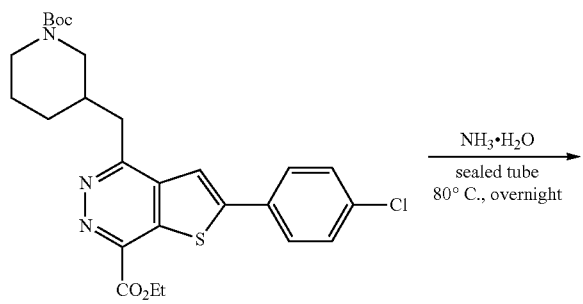

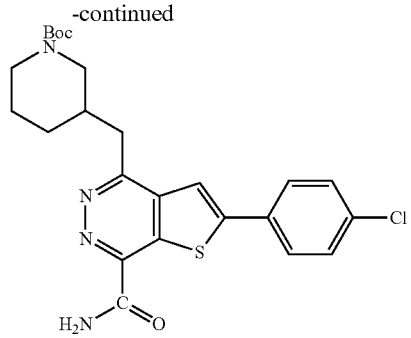

A mixture of 4-(1-Boc-3-piperidinemethy)-2-(4-chlorophenyl)-thieno[2,3-d]pyridazine-7-carboxylic acid ethyl ester (0.3 g), dioxane (5 ml) and NH3.H2O (5 ml) was heated at 80° C. over night. The reaction was cooled and solvent was removed under vacuum. The residue was purified by flash chromatography (silica gel, PE:EA=5:1) to obtain 4-(1-Boc-3-piperidinemethy)-2(4-chlorophenyl)-thieno[2,3-d]pyridazine-7-carboxylic acid amide 0.22 g as a solid.

1HNMR (500 MHz, CDCl$_3$), δ 8.10 (s, 1H), 0.77 m, H), 0.66 s, H), 0.48 m, 2H), 5.90 (s, 1H), 4.05 (s, 1H), 3.88 (m, 1H), 3.31 (m, 1H), 3.21 (m, 1H), 2.81 (m, 2H), 2.28 (s, 1H), 1.81 (s, 1H), 1.67 (s, 3H), 1.39 (s, 9H).

MS (ESI): 487 (M+1)

Step 11: 2-(4-chlorophenyl)-4-(3-piperidinemethy)-thieno[2,3-d]pyridazine-7-carboxylic acid amide hydrochloric acid

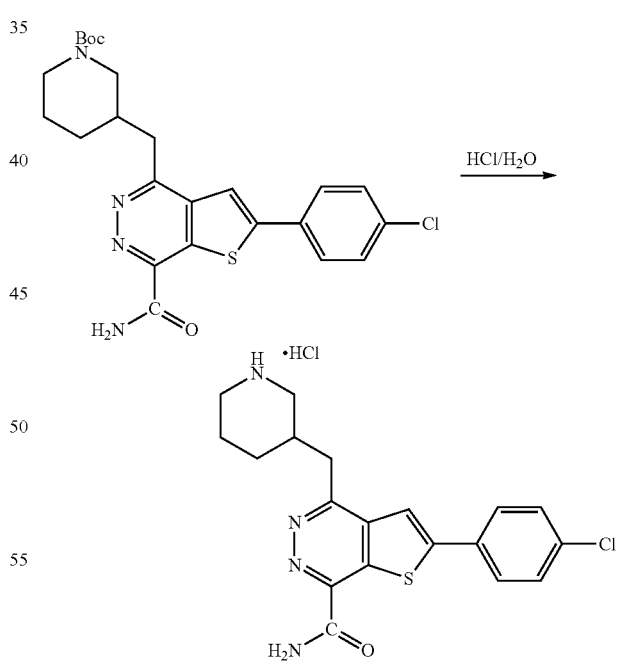

To a solution of 4-(1-Boc-3-piperidinemethy)-2(4-chlorophenyl)-thieno 2,3-d]pyridazine-7-carboxylic acid amide (200 g) in ethyl acetate (4 ml) was added HCl 4 ml, 3M) at 30° C. for 1 h. The reaction was concentrated under reduced pressure to give 2-(4-chlorophenyl)-4-(3-piperidinemethy)-thieno[2,3-d]pyridazine-7-carboxylic acid amide hydrochloric acid as a solid (100 mg).

1HNMR (500 MHz, DMSO), δ 9.51 (m, 1H), 9.09 (m, 1H), 8.79 (s, 1H), 8.66 (s, 1H), 8.29 (s, 1H), 8.08 (m, 2H), 7.62 (m, 2H), 3.45 (m, 2H), 3.4 (m, 1H), 3.17 (m, 1H), 2.79 (m, 2H), 2.52 (m, 1H), 1.81 (m, 2H), 1.77 (m, 1H), 1.42 (m, 1H).

MS (ESI):387 (M+1).

Step 12: 2-(4-chlorophenyl)-4-(3-piperidinemethy)-thieno[2,3-d]pyridazine-7-carboxylic acid amide

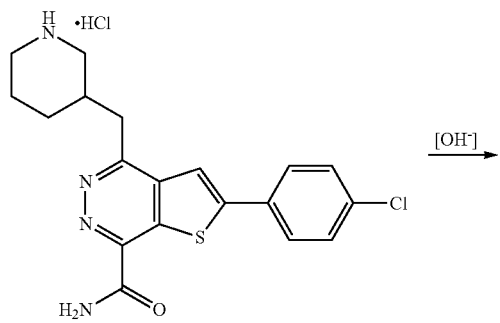

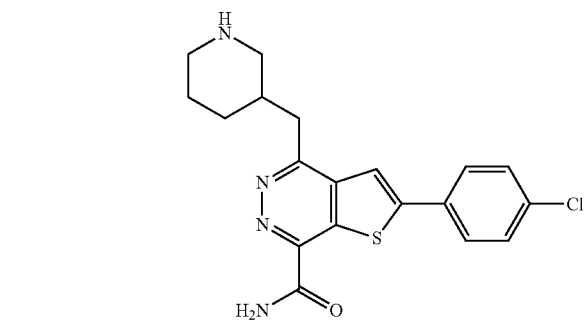

A solution of 2-(4-chlorophenyl)-4-(3-piperidinemethy)-thieno[2,3-d]pyridazine-7-carboxylic acid amide hydrochloric acid (100 mg) in H$_2$O was basified by Na$_2$CO$_3$ to pH=9-10. The mixture was extracted by ethyl acetate, washed with water, and concentrated to obtained 2-(4-chlorophenyl)-4-(3-piperidinemethy)-thieno[2,3-d]pyridazine-7-carboxylic acid amide 70 mg.

Example 2

2-(4-chlorophenyl)-4-(3-tetrahydropyranmethy)-thieno[2,3-d]pyridazine-7-carboxylic acid amide

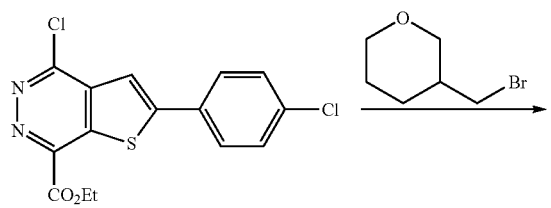

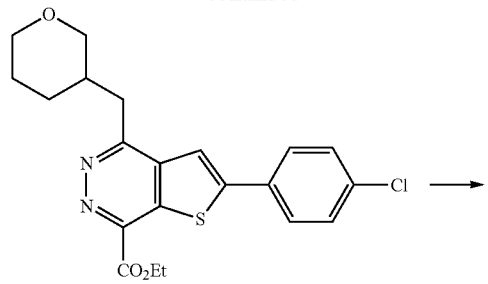

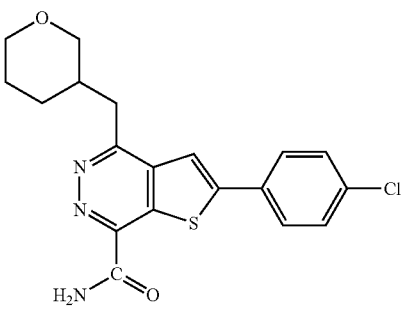

Step 1

A mixture of 3-(Bromomethyl)Tetrahydro-2H-Pyran (24.75 g, 0.138 mol), DMPU (225 ml), FeCl3 (0.75 g) and CuCl (0.3 g) was slowly added Et$_2$Zn (106.8 ml) by drop-wise at 40~45° C. for 45 minutes to get the zinc-reagent.

To a mixture of 4-chloro-2-(4-chlorophenyl)-thieno[2,3-d]pyridzaine-7-carboxylic acid ethyl ester, THF (810 ml) and PdCl2(dppf) (5.09 g) was added zinc-reagent mentioned above at 40~45° C. for 4 hours. The reaction was poured into saturated brine and filtrated after stirring for 15 minutes; the aqueous fraction was washed by THF (500 ml, 2x). The organic layer and the extract were washed with saturated brine and dried over anhydrous Na$_2$SO$_4$ over night. The organic layer was concentrated under reduced pressure to give 2-(4-chlorophenyl)-4-(3-tetrahydropyranmethy)-thieno[2,3-d]pyridazine-7-carboxylic acid ethyl ester (25 g).

MS (ESI): 417 (M+1).

Step 2

A mixture of 2-(4-chlorophenyl)-4-(3-tetrahydropyranmethy)-thieno[2,3-d]pyridazine-7-carboxylic acid ethyl ester (3 g), 1,4-dioxane 5 ml and ammonia 5 ml was heated at 80° C. overnight. The reaction was cooled to room temperature and diluted with ethyl acetate, the aqueous washed with ethyl acetate. The combined ethyl acetate layer and adjusted with 1M HCl to pH=3, then washed with saturated brine to pH=7 and dried over anhydrous Na$_2$SO$_4$. The organic layer was concentrated under reduced pressure to give 2-(4-chlorophenyl)-4-(3-tetrahydropyranmethy)-thieno[2,3-d]pyridazine-7-carboxylic acid amide (2 g).

MS (ESI): 388 (M+1)

Example 3

2-(4-chlorophenyl)-4-(3-tetrahydrothiapyranmethyl)-thieno[2,3-d]pyridazine-7-carboxylic acid amide

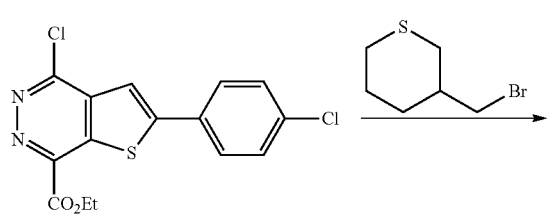

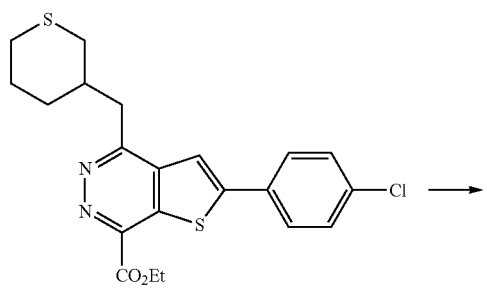

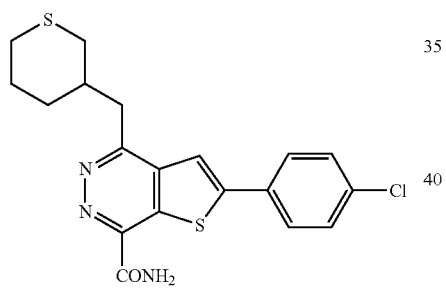

Step 1

Using the procedure described in Example 2 (step 1) but replacing 3-(Bromomethyl)Tetrahydro-2H-Pyran with 3-(Bromomethyl)Tetrahydro-2H-thiapyran provided the compound 2-(4-chlorophenyl)-4-(3-tetrahydrothiapyran methyl)-thieno[2,3-d]pyridazine-7-carboxylic acid ethyl ester.

Step 2

Using the procedure described in Example 2 (step 2) but replacing 2-(4-chlorophenyl)-4-(3-tetrahydropyranmethy)-thieno[2,3-d]pyridazine-7-carboxylic acid ethyl ester with 2-(4-chlorophenyl)-4-(3-tetrahydrothiapyran methyl)-thieno[2,3-d]pyridazine-7-carboxylic acid ethyl ester provided the title compound.

MS (ESI): 433 (M+1).

Example 4

2-(4-chlorophenyl)-4-(2-piperidinemethy)-thieno[2,3-d]pyridazine-7-carboxylic acid amide

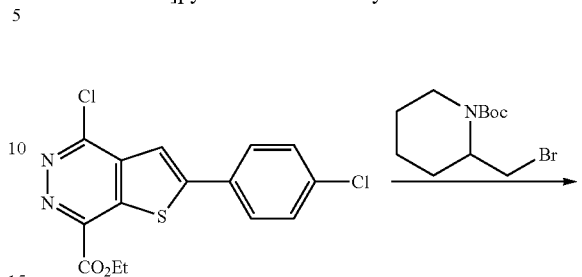

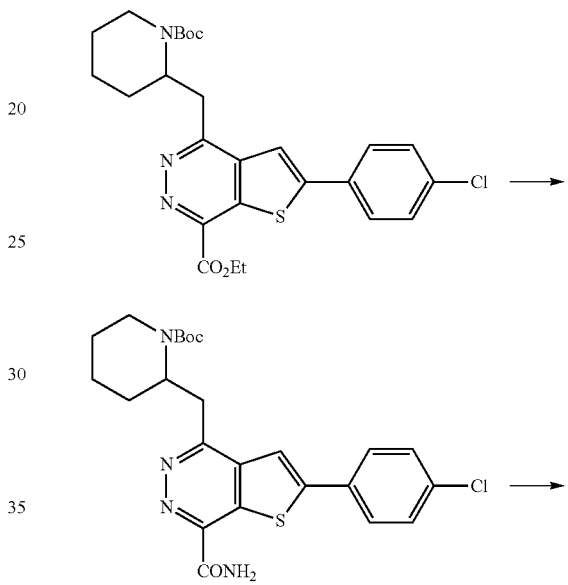

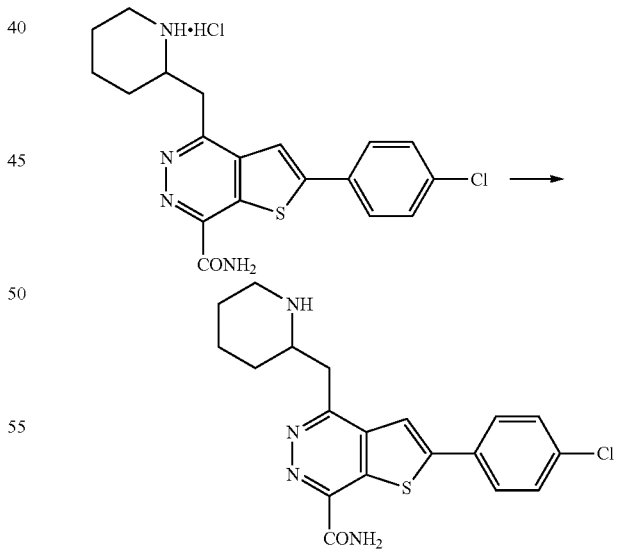

Step 1

Using the procedure described in Example 2 (step 1) but replacing 3-(Bromomethyl)Tetrahydro-2H-Pyran with N-Boc-2-bromomethylpiperidine provided the compound 4-(1-Boc-2-piperidinemethy)-2-(4-chlorophenyl)-thieno[2,3-d]pyridazine-7-carboxylic acid ethyl ester. MS (ESI): 516 (M+1).

Step 2

Using the procedure described in Example 1 (step 10) but replacing 4-(1-Boc-3-piperidinemethy)-2-(4-chlorophenyl)-thieno[2,3-d]pyridazine-7-carboxylic acid ethyl ester with 4-(1-Boc-2-piperidinemethy)-2-(4-chlorophenyl)-thieno[2,3-d]pyridazine-7-carboxylic acid ethyl ester provided the compound 4-(1-Boc-2-piperidinemethy)-2-(4-chlorophenyl)-thieno[2,3-d]pyridazine-7-carboxylic acid amide. MS (ESI): 487 (M+1).

Step 3

Using the procedure described in Example 1 (step 11) but replacing 4-(1-Boc-3-piperidinemethy)-2-(4-chlorophenyl)-thieno[2,3-d]pyridazine-7-carboxylic acid amide with 4-(1-Boc-2-piperidinemethy)-2-(4-chlorophenyl)-thieno[2,3-d]pyridazine-7-carboxylic acid amide provided the compound 2-(4-chlorophenyl)-4-(2-piperidinemethy)-thieno[2,3-d]pyridazine-7-carboxylic acid amide hydrochloric acid. MS (ESI): 423 (M+1).

Step 4

Using the procedure described in Example 1 (step 12) but replacing 4-(1-Boc-3-piperidinemethy)-2-(4-chlorophenyl)-thieno[2,3-d]pyridazine-7-carboxylic acid amide hydrochloric acid with 4-(1-Boc-2-piperidinemethy)-2-(4-chlorophenyl)-thieno[2,3-d]pyridazine-7-carboxylic acid amide hydrochloric acid provided the title compound. MS (ESI): 387 (M+1).

Example 5

2-(4-chlorophenyl)-4-(4-piperidinemethy)-thieno[2,3-d]pyridazine-7-carboxylic acid amide

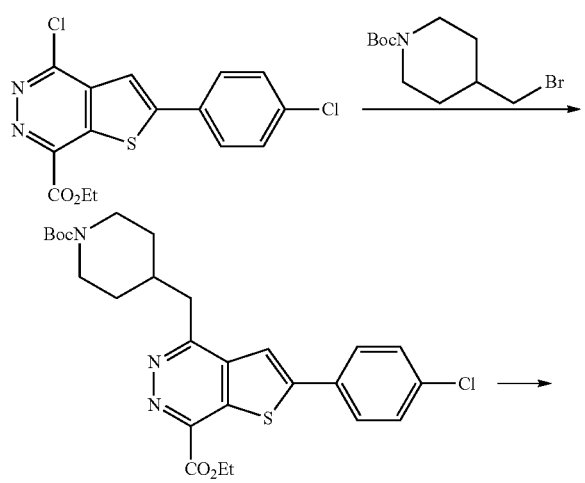

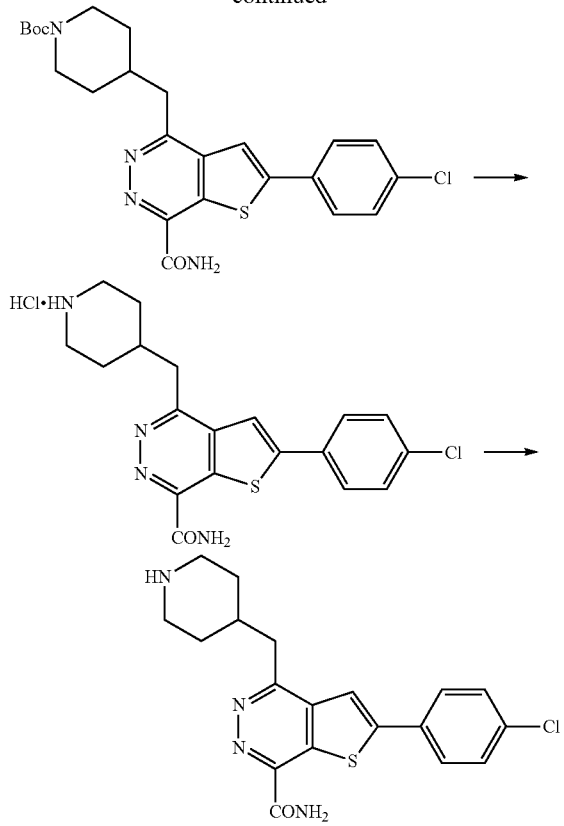

Using the procedure described in Example 4 but replacing N-Boc-2-bromomethylpiperidine with N-Boc-4-bromomethylpiperidine provided the title compound. MS (ESI): 387 (M+1).

Example 6

2-(4-chlorophenyl)-4-(3-pyrrolidinemethy)-thieno[2,3-d]pyridazine-7-carboxylic acid amide Using the procedure described in Example 4 but replacing N-Boc-2-bromomethylpiperidine with N-Boc-3-bromomethypyrrolidine provided the title compound.

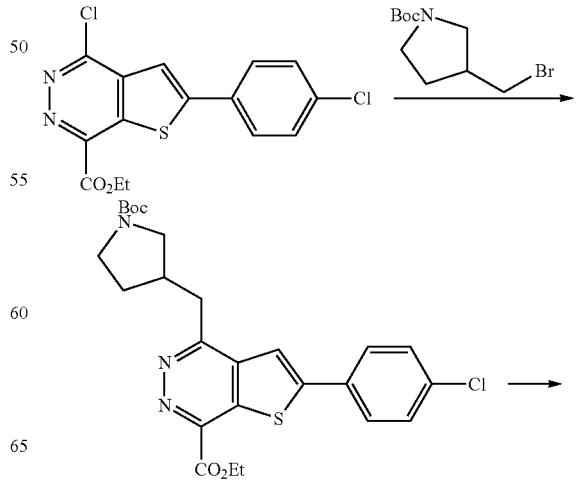

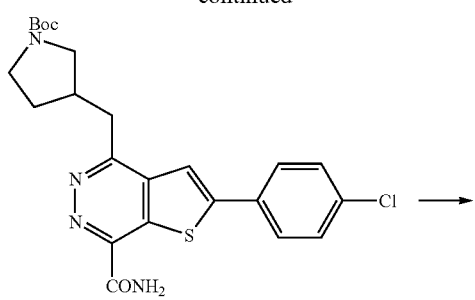

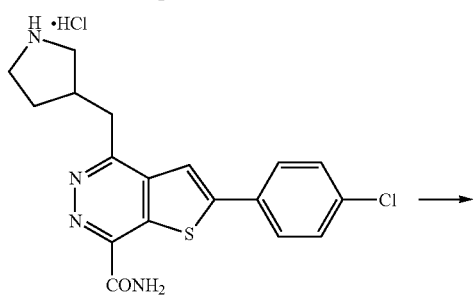

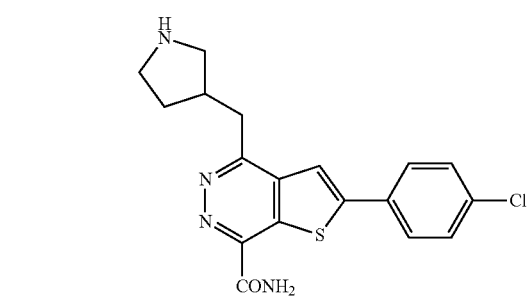

MS (ESI): 373 (M+1)

Example 7

2-(4-chlorophenyl)-4-(3-tetrahydrofuranmethy)-thieno[2,3-d]pyridazine-7-carboxylic acid amide

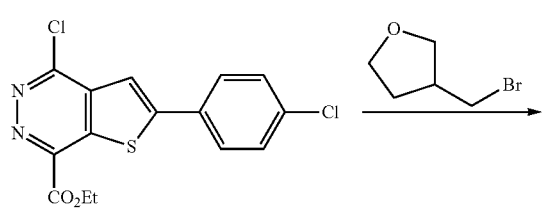

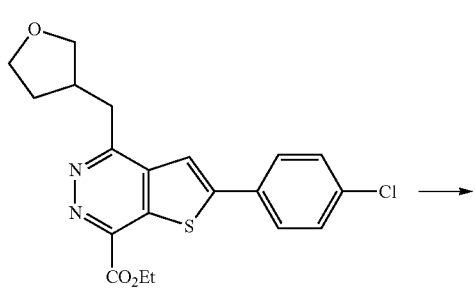

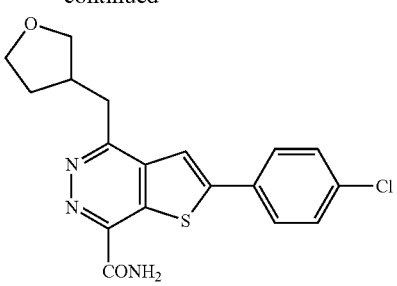

Using the procedure described in Example 2 but replacing 3-(bromomethyl)tetrahydro-2H-pyran with 3-(bromomethyl)-tetrahydrofuran provided the title compound. MS (ESI): 374 (M+1).

Example 8

2-(4-chlorophenyl)-4-(3-tetrahydrothiophenemethy)-thieno[2,3-d]pyridazine-7-carboxylic acid amide

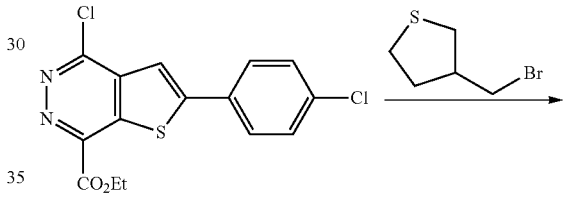

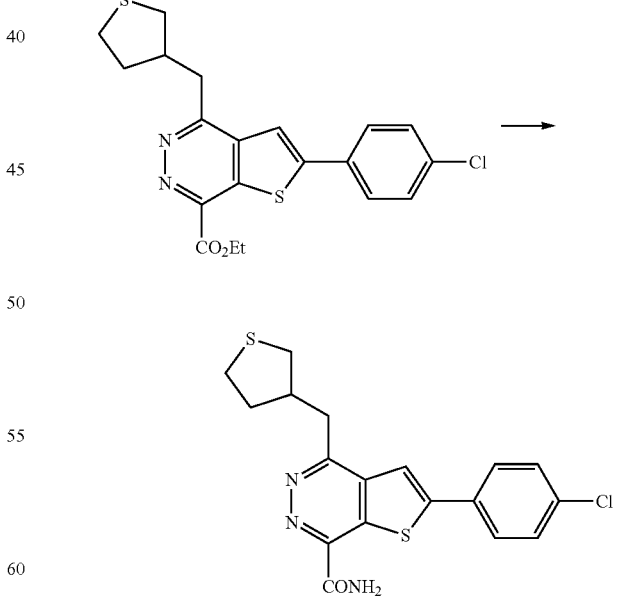

Using the procedure described in Example 2 but replacing 3-(bromomethyl)tetrahydro-2H-pyran with 3-(bromomethyl)-tetrahydrothiophene provided the title compound. MS (ESI): 389 (M+1).

Example 9

2-(4-chlorophenyl)-4-(3-pyridinemethy)-thieno[2,3-d]pyridazine-7-carboxylic acid amide

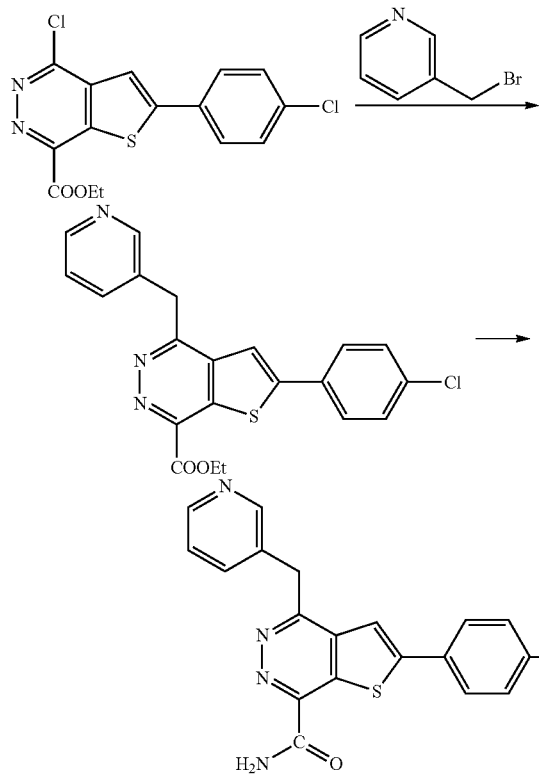

Using the procedure described in Example 2 but replacing 3-(bromomethyl)tetrahydro-2H-pyran with 3-(bromomethyl)-pyridine provided the title compound. MS (ESI): 381 (M+1).

Example 10

2-(4-chlorophenyl)-4-(3-α-pyranmethy)-thieno[2,3-d]pyridazine-7-carboxylic acid amide

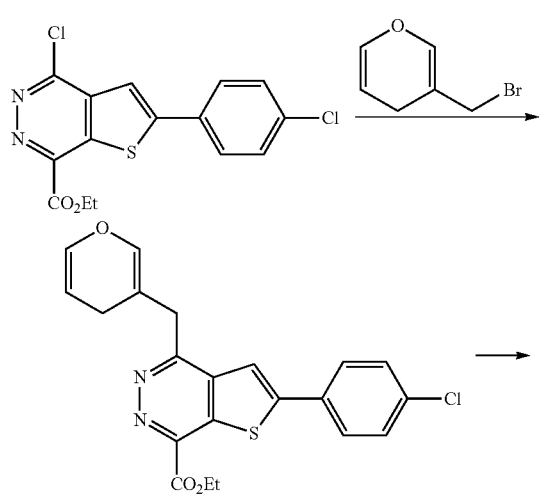

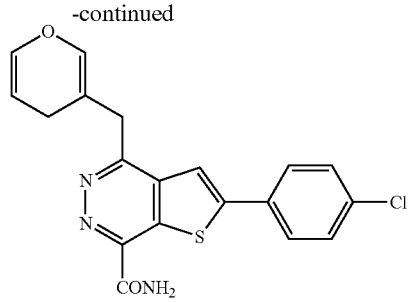

Using the procedure described in Example 2 but replacing 3-(bromomethyl)tetrahydro-2H-pyran with 3-(bromomethyl)-pyran provided the title compound. MS (ESI): 383 (M+1).

Example 11

2-(4-chlorophenyl)-4-(3-α-thiapyranmethy)-thieno[2,3-d]pyridazine-7-carboxylic acid amide

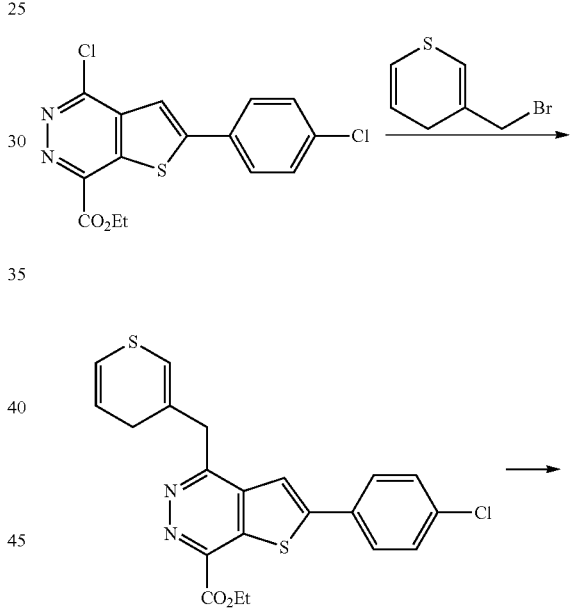

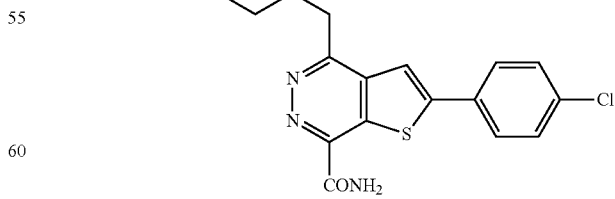

Using the procedure described in Example 2 but replacing 3-(bromomethyl)tetrahydro-2H-pyran with 3-(bromomethyl)-thiapyran provided the title compound. MS (ESI): 399 (M+1).

Example 12

2-(4-chlorophenyl)-4-(2-pyridinemethy)-thieno[2,3-d]pyridazine-7-carboxylic acid amide

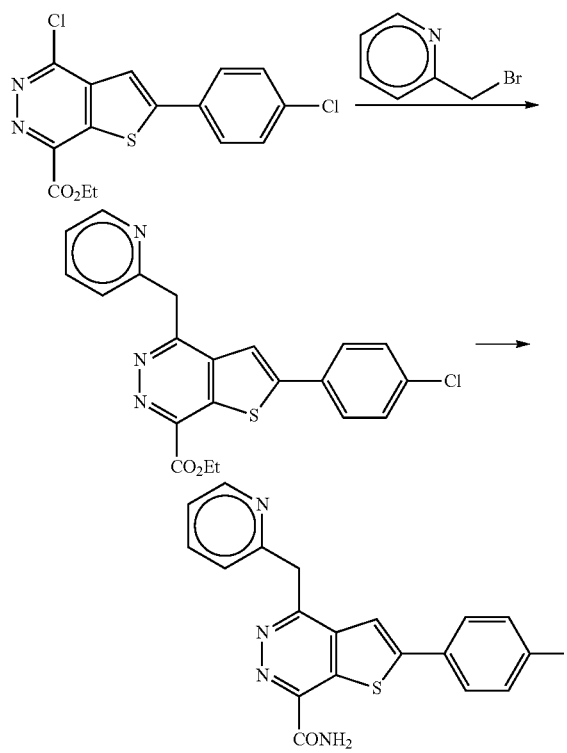

Using the procedure described in Example 2 but replacing 3-(bromomethyl)tetrahydro-2H-pyran with 2-(bromomethyl)-pyridine provided the title compound.
MS (ESI): 381 (M+1)

Example 13

2-(4-chlorophenyl)-4-(4-pyridinemethy)-thieno[2,3-d]pyridazine-7-carboxylic acid amide

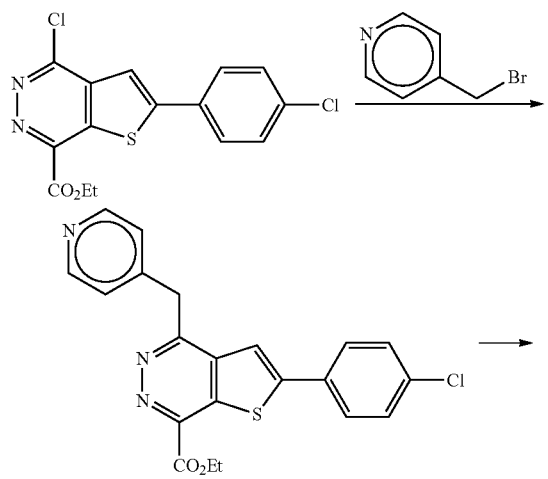

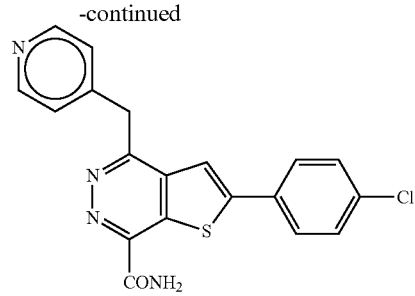

Using the procedure described in Example 2 but replacing 3-(bromomethyl)tetrahydro-2H-pyran with 4-(bromomethyl)-pyridine provided the title compound. MS (ESI): 381 (M+1).

Example 14

2-(4-chlorophenyl)-4-(3-pyrrolemethy)-thieno[2,3-d]pyridazine-7-carboxylic acid amide

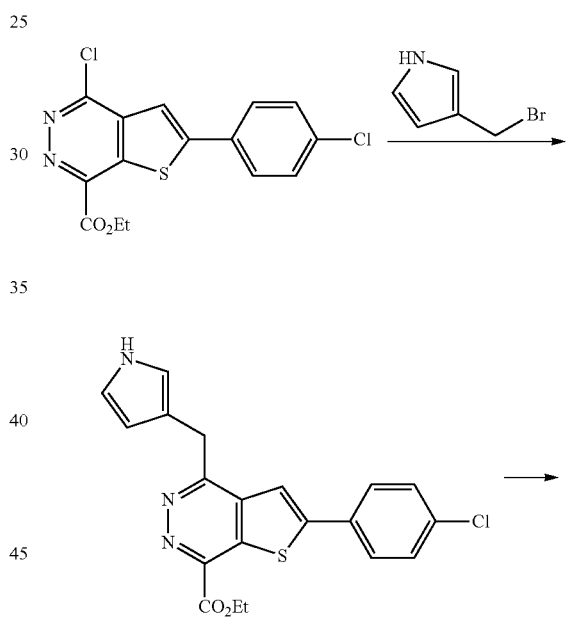

Using the procedure described in Example 2 but replacing 3-(bromomethyl)tetrahydro-2H-pyran with 3-(bromomethyl)-pyrrole provided the title compound. MS (ESI): 369 (M+1).

Example 15

2-(4-chlorophenyl)-4-(3-furanmethy)-thieno[2,3-d]pyridazine-7-carboxylic acid amide

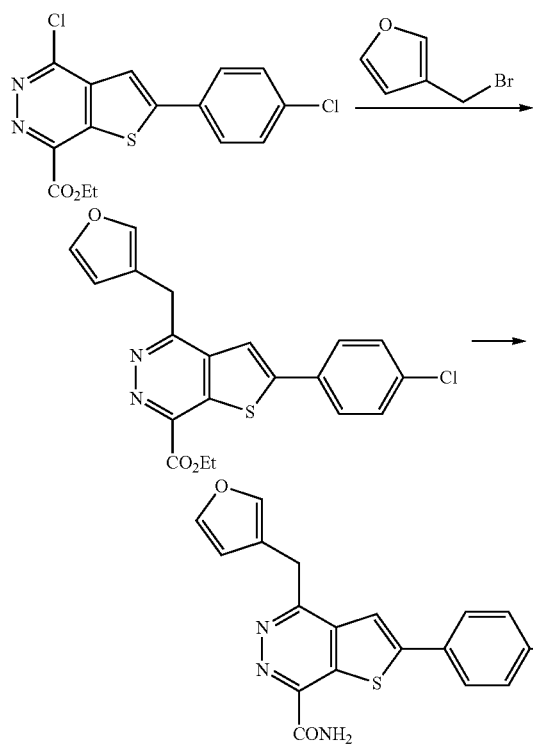

Using the procedure described in Example 2 but replacing 3-(bromomethyl)tetrahydro-2H-pyran with 3-(bromomethyl)-furan provided the title compound. MS (ESI): 370 (M+1).

Example 16

2-(4-chlorophenyl)-4-(3-thiaphenemethy)-thieno[2,3-d]pyridazine-7-carboxylic acid amide

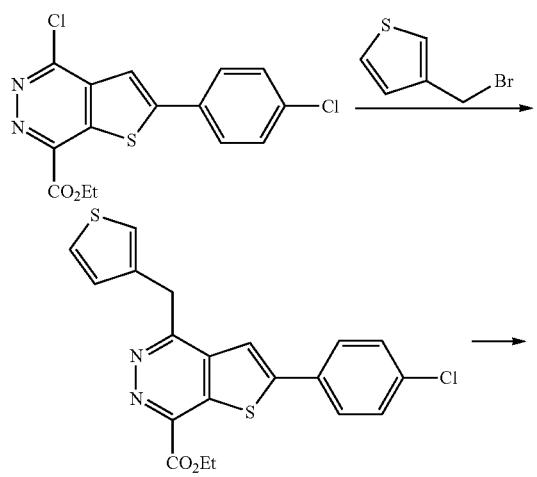

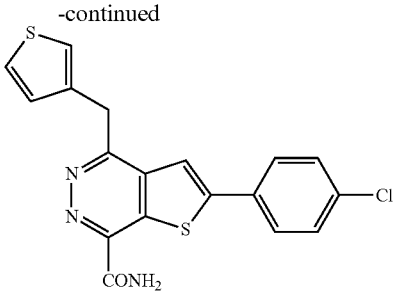

Using the procedure described in Example 2 but replacing 3-(bromomethyl)tetrahydro-2H-pyran with 3-(bromomethyl)-thiaphene provided the title compound. MS (ESI): 386 (M+1).

Example 17

2-(4-chlorophenyl)-4-(2-pyrrolemethy)-thieno[2,3-d]pyridazine-7-carboxylic acid amide

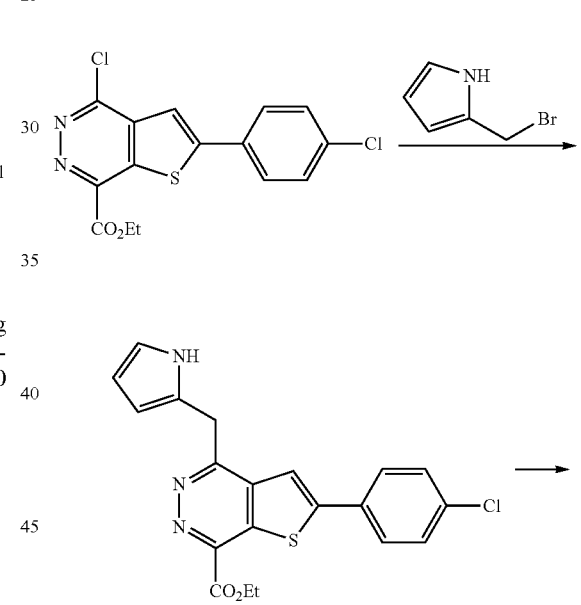

Using the procedure described in Example 2 but replacing 3-bromomethyl)tetrahydro-2H-pyran with 2-(bromomethyl)-pyrrole provided the title compound. MS (ESI): 369 (M+1).

Example 18

2-(3,5-dichlorophenyl)-4-(3-piperidinemethyl)-thieno-[2,3-d]pyridazine-7-carboxylic acid amide

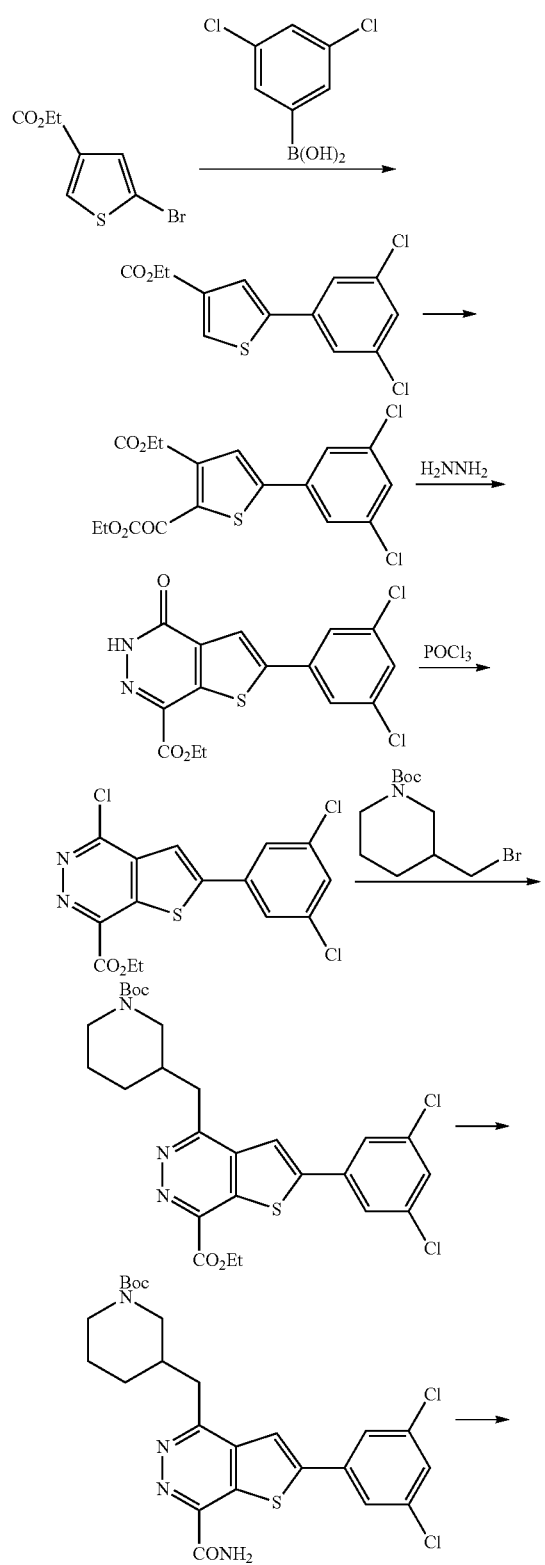

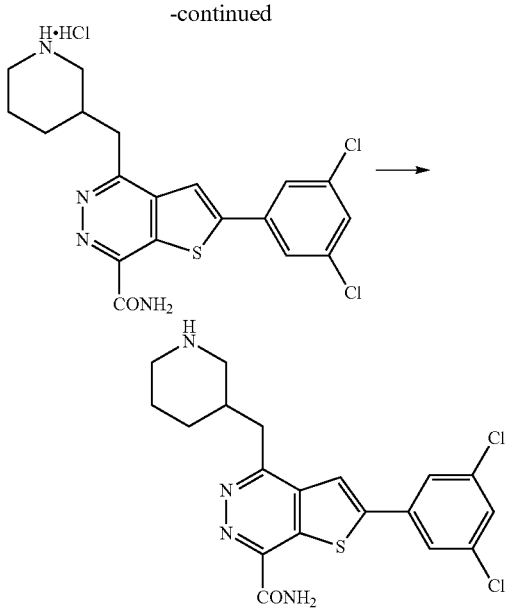

Step 1: 5-(3,5-dichlorophenyl)-3-thiophene carboxylic acid ethyl ester

Using the procedure described in Example 1 (step 4) but replacing 4-chlorophenylboronic acid with 3,5-dichlorobenzene boronic acid provided the title compound.

Step 2: 5-(3,5-dichlorophenyl)-2-thiophene-3-carboxylic acid ethyl ester

Using the procedure described in Example 1 (step 5) but replacing 5-(4-chlorophenyl)-3-thiophene carboxylic acid ethyl ester with 5-(3,5-dichlorophenyl)-3-thiophene carboxylic acid ethyl ester provided the title compound.

Step 3: 2-(3,5-dichlorophenyl)-4-oxo-4,5-dihydro-thiero[2,3-d]pyridazine-7-carboxyllic acid ethyl ester Using the procedure described in Example 1 (step 6) but replacing 5-(4-chlorophenyl)-2-thiophene-3-carboxylic acid ethyl ester with 5-(3,5-dichlorophenyl)-2-thiophene-3-carboxylic acid ethyl ester provided the title compound.

Step 4: 4-chloro-2-(3,5-dichlorophenyl)-thieno[2,3-d]pyridzaine-7-carboxylic acid ethyl ester Using the procedure described in Example 1 (step 7) but replacing 2-(4-chlorophenyl)-4-oxo-4,5-dihydro-thiero[2,3-d]pyridazine-7-carboxyllic acid ethyl ester with 2-(3,5-dichlorophenyl)-4-oxo-4,5-dihydro-thiero[2,3-d]pyridazine-7-carboxyllic acid ethyl ester provided the title compound.

Step 5: 2-(3,5-dichlorophenyl)-4-(N-boc-3-piperidinemethyl)-thiophene[2,3-d]pyridazine-7-carboxylic acid ethyl ester Using the procedure described in Example 4 (step 1) but replacing 4-chloro-2-(4-chlorophenyl)-thieno[2,3-d]pyridzaine-7-carboxylic acid ethyl ester and N-Boc-2-bromomethylpiperidine with 4-chloro-2-(3,5-dichlorophenyl)-thieno[2,3-d]pyridzaine-7-carboxylic acid ethyl ester and N-Boc-3-bromomethylpiperidine provided the title compound.

Step 6: 4-(1-Boc-3-piperidinemethy)-2-(3,5-dichlorophenyl)-thieno[2,3-d]pyridazine-7-carboxylic acid ethyl ester Using the procedure described in Example 1 (step 10) but replacing 2-(4-chlorophenyl)-4-(N-boc-3-piperidinemethyl)-thiophene[2,3-d]pyridazine-7-carboxylic acid ethyl ester with 2-(3,5-dichlorophenyl)-4-(N-boc-3-piperidinemethyl)-thiophene[2,3-d]pyridazine-7-carboxylic acid ethyl ester provided the title compound.

Step 7: 2-(3,5-dichlorophenyl)-4-(3-piperidinemethy)-thieno[2,3-d]pyridazine-7-carboxylic acid amide hydrochloric acid Using the procedure described in Example 1 (step 11) but replacing 4-(1-Boc-3-piperidinemethy)-2-(4-chlorophenyl)-thieno[2,3-d]pyridazine-7-carboxylic acid ethyl ester with 4-(1-Boc-3-piperidinemethy)-2-(3,5-dichlorophenyl)-thieno[2,3-d]pyridazine-7-carboxylic acid ethyl ester provided the title compound.

Step 8: 2-(3,5-dichlorophenyl)-4-(3-piperidinemethyl)-thieno-[2,3-d]pyridazine-7-carboxylic acid amide Using the procedure described in Example 1 (step 12) but replacing 2-(4-chlorophenyl)-4-(3-piperidinemethy)-thieno[2,3-d]pyridazine-7-carboxylic acid amide hydrochloric acid with 2-(3,5-dichlorophenyl)-4-(3-piperidinemethy)-thieno[2,3-d]pyridazine-7-carboxylic acid amide hydrochloric acid provided the title compound. MS (ESI): 421 (M+1).

Example 19

Formulations

Pharmaceutical preparations for delivery by various routes are formulations as shown in the following. "Active ingredient" or "Active compound" as used in the following means one or more of the compounds of formula I.

1. Parenteral injection. Formulation: Active ingredient, 50 g; Sodium chloride, 2250 g; Water for injection add to 250,000 ml, to make 1,000 bottles.

Preparation: The active ingredient is dissolved in a portion of water for injection; a sufficient quantity of sodium chloride is then added with stirring to make the solution isotonic. Its pH is adjusted to 4.0 to 5.0. activated carbon (250 g) was added to for 30 min before removed with Filter decarbonization. The mixture was then bottling in 250 ml every bottle after precision filtration with Titanium Rod. After 115° C. sterile water bath the parenteral injection was prepared.

2. Pellet. Formulation: Active ingredient, 50 g; Starch, 160 g; Hydroxypropyl cellulose, 39 g; Polyvidone K30, q.s.; Sodium carboxymethyl starch, 10.4 g; Magnesium stearate, 1.3 g; for making 1000 tablets.

Preparation: Active ingredient, starch and Hydroxypropyl cellulose were put in the hopper of a fluid bed granulator and warmed to 38-60° C. Polyvidone K30 water solution was nebulized to granulate the mixture. The mixture was then dried at 55-60° C. for 10 min, mixed with sodium carboxymethyl starch and magnesium stearate to tabletting.

Capsule. Formulation: Active ingredient, 50 g; Lactose, 194.4 g; Sodium carboxymethylstarch, 7.8 g; Silion Dioxide, 5.2 g; Magnesium stearate, 2.6 g.

Preparation: Mix active ingredient, Lactose, sodium carboxymethylstarch and Silion Dioxide in the mixer for 1 h and then added magnesium stearate for another 10 min before filled in Gelatin plastic shell.

Example 20

Toxicity, In Vitro and In Vivo Effectiveness Tests

Some of the above compounds were tested in vitro or in vivo for their anti-cancer or anti-tumor activities. These tests include cellular toxicity tests using SRB and MTT methods for 72 hours, and the results are summarized in Table 1. The effect on inhibiting mouse S180 sarcoma was summarized in Table 2, and the effects on treating transplanted human colon cancer HT-99 on nude mice are summarized in Table 3.

TABLE 1

In vitro anti-cancer cell activities IC$_{50}$ (µM)

| Compound No. | Human Gastric Cancer (BGC-823) | Human colon cancer HT-29 | Mouse Lung Cancer (3LL) | Human Ovarian cancer (A2780) |
| --- | --- | --- | --- | --- |
| 1 | 3.35 | 4.22 | 1.40 | 6.40 |
| 2 | 4.47 | 7.4 | 3.32 | 6.20 |
| 6 | 5.86 | 7.53 | 2.55 | 1.54 |
| 11 | 9.24 | 10.70 | 8.43 | 11.85 |
| 13 | 2.62 | 0.73 | 1.24 | 1.18 |
| 14 | 30.46 | 16.76 | 8.59 | 6.01 |
| 15 | 2.25 | | 804 | |
| 21 | | 8.68 | | |
| 23 | >100 | 5.57 | >100 | >100 |
| 24 | 24.58 | >100 | >100 | >100 |
| 34 | 74.50 | >100 | 50.64 | >100 |
| 38 | 8.17 | 1.33 | 3.13 | 3.13 |
| 46 | 11.11 | >100 | >100 | 30.29 |
| 58 | 16.4 | 21.8 | 21.4 | 13.9 |
| 69 | 17.02 | 9.48 | 3.31 | 7.11 |
| 70 | 5.45 | >100 | >100 | >100 |

TABLE 2

Inhibitive Activities of Mouse S180 (N = 7, X ± SD)

| Compound No. | Dosage (mg/kg) | Admin Route | Starting Body Weight (g) | Ending Body Weight (g) | Tumor Weight (g) | Body Weight without Tumor (g) | Inhibition Rate (%) |
|---|---|---|---|---|---|---|---|
| 2 | 50 | ip | 19.70 ± 0.76 | 20.03 ± 1.11 | 1.41 ± 0.30 | 18.63 ± 0.93 | 52.62 |
| 20 | 50 | ip. | 19.50 ± 0.89 | 21.19 ± 1.40 | 1.86 ± 0.26 | 19.33 ± 1.60 | 37.23 |
| 12 | 50 | ip. | 19.50 ± 0.73 | 20.79 ± 1.83 | 1.48 ± 0.16 | 19.31 ± 1.79 | 50.02 |
| 24 | 50 | ip | 19.39 ± 0.60 | 23.18 ± 1.66 | 1.62 ± 0.26 | 21.56 ± 1.48 | 45.45 |
| Negative Control | | | 19.49 ± 0.76 | 26.21 ± 2.38 | 2.97 ± 0.63 | 23.24 ± 2.18 | |

Note:
ip = intra-peritoneal injection

TABLE 3

Effects on HT99 Transplanted Nude Mice

| Compound # | Dosage (mg/kg) | Admin. Route | No. of Animals d0/dn | TV (X ± SD, mm³) d0 | TV (X ± SD, mm³) dn | RTV X ± SD | T/C (%) |
|---|---|---|---|---|---|---|---|
| 2 | 60 | ip, d0, 1 | 6/3 | 146 ± 13 | 690 ± 271 | 4.64 ± 1.65 | 70 |
| 5 | 60 | ip, d0, 1 | 6/3 | 150 ± 16 | 910 ± 0 | 6.40 ± 0 | 96.5 |
| 11 | 60 | ip, d0, 1 | 6/1 | 150 ± 15 | 1224 ± 440 | 7.52 ± 0.26 | 113.4 |
| 19 | 60 | ip, d0, 1 | 6/3 | 147 ± 9 | 663 ± 86 | 4.53 ± 0.82 | 68.3 |
| 22 | 60 | ip, d0, 1 | 6/3 | 151 ± 11 | 714 ± 127 | 4.69 ± 0.71 | 70.7 |
| 30 | 60 | ip, d0, 1 | 6/3 | 144 ± 23 | 482 ± 83 | 3.78 ± 1.09 | 57.0 |
| 31 | 60 | ip, d0, 1 | 6/3 | 145 ± 13 | 785 ± 300 | 5.36 ± 1.94 | 80.8 |
| GCT + 2 | 20 + 25 | ip + iv, d0, 1 | 6/6 | 183 ± 7 | 409 ± 81 | 1.58 ± 0.27 | 30 |
| GCT + 11 | 20 + 25 | ip + iv, d0, 1 | 6/6 | 196 ± 15 | 399 ± 89 | 1.55 ± 0.22 | 27 |
| GCT | 20 | ip, d0, 1 | 6/6 | 184 ± 17 | 463 ± 74 | 1.64 ± 0.44 | 37 |
| CPT-11 + 2 | 20 + 25 | ip + iv, d0, 1 | 6/4 | 193 ± 15 | 619 ± 115 | 3.80 ± 1.01 | 57 |
| CPT-11 + 11 | 20 + 25 | ip + iv, d0, 1 | 6/5 | 207 ± 13 | 601 ± 36 | 1.61 ± 0.57 | 33 |
| ADR + 2 | 4 + 25 | ip + iv, d0, 1 | 6/3 | 195 ± 19 | 573 ± 80 | 3.63 ± 1.09 | 50 |
| ADR + 11 | 4 + 25 | ip + iv, d0, 1 | 6/3 | 180 ± 21 | 697 ± 64 | 4.60 ± 1.52 | 69 |
| ADR | 4 | ip, d0, 1 | 6/3 | 183 ± 13 | 667 ± 67 | 4.38 ± 1.38 | 64 |
| Neg. Ctrl. | solvent | ip, d0, 1 | 10/8 | 154 ± 12 | 1022 ± 276 | 6.63 ± 1.62 | |

Notes:
d0, 0 days after drug treatment;
dn, 17 days after drug treatment;
RTV relative tumor volume.
Contro group n = 10,
treatment group n = 6.
ip: intra-peritoneal injection;
iv: intra-venal injection;
positive controls: GCT = Gemcitabine, ADR = adriamycin ®, and CPT-11 = irinotecan.

The data above show that the compounds of the present invention have anti-tumor effects, and can also enhance the anti-tumor effects of other compounds such as GCT, CPT-11, ADR.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A method for treating a cancer that can be treated by inhibition of checkpoint protein kinase CHK1 or CHK2, wherein the cancer is selected from the group consisting of gastric cancer, colon cancer, lung cancer, ovarian cancer, and sarcoma, the method comprising administering to a patient in need thereof a pharmaceutical composition comprising a pharmaceutically acceptable excipient and a therapeutically effective amount of a compound of formula I:

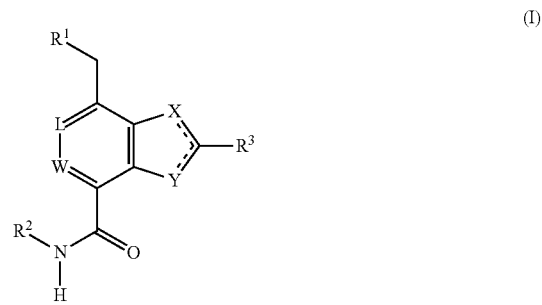

in the form of a racemate, a pure stereoisomer, or in the form of a mixture of stereoisomers in any mixing ratio, in the illustrated form or in the form of a salt, wherein,
X=CH, N, S, O;
Y=CH, S, N, O;
W=CH, N, CR$^{20}$;
L=CH, N, CR$^{20}$;
where R$^{20}$ is selected from —OR$^{21}$; —NR$^{21}$R$^{22}$; —CN; —SR$^{21}$; —S(O)R$^{21}$; —S(O)$_2$R$^{21}$; —S(O)$_2$NR$^{21}$R$^{22}$; —C(O)NR$^{21}$R$^{22}$; —N(R$^{21}$)C(O)R$^{22}$; —N(R$^{21}$)S(O)2R$^{22}$; —N(R$^{21}$)C(O)N(R$^{22}$R$^{23}$); —N(R$^{21}$)C(O)OR$^{22}$; F; Cl; Br; I; alkyl (C$_1$-C$_8$); cycloalkyl (C$_3$-C$_8$) without and with substitutions by alkyls (C$_1$-C$_8$), cycloalkyls (C$_3$-C$_8$), aryls, heteroaryls; aryl with or without substitution; heteroaryl with or without substitution; aryalkyl with or without substitution; heterocyclyl with or without substitution; heteterocyclylalkyl with or without substitution; alkenyl with or without substitution; alkynyl with or without substitution;
wherein R$^{21}$, R$^{22}$ and R$^{23}$ is independently chosen from H, alkyl (C$_1$-C$_8$), cycloalkyls (C$_3$-C$_8$), aryl with or without substitution, alkylaryl with or without substitutions, heteroaryl with or without substitution:
R$^1$ is selected from following groups:

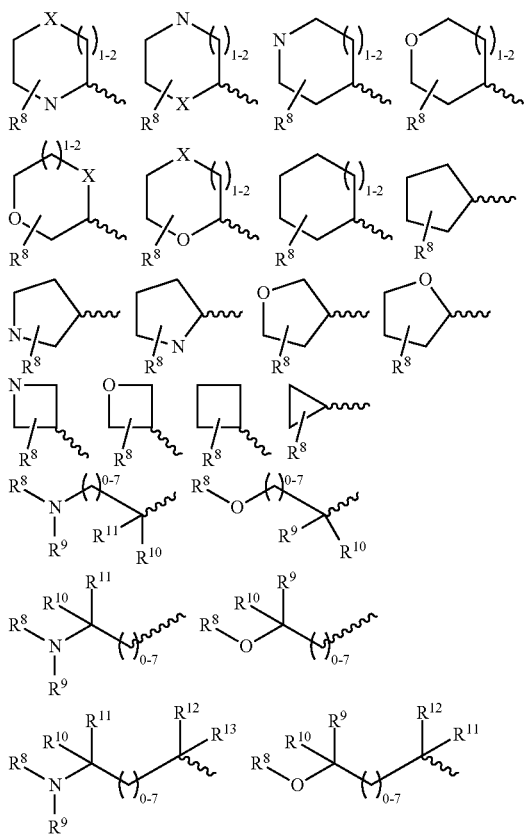

where X=CH$_2$, NH, S, or O;
R$^8$=—H, —NH$_2$, —OH, —N(R$^4$, R$^5$), —C(R$^4$R$^5$)$_{1-7}$NR$^6$R$^7$, —C(R$^4$R$^5$)$_{1-7}$OR$^6$, —N(R$^4$)NR$^5$R$^6$
R$^4$, R$^5$, R$^6$, R$^7$=H, alkyls (C$_1$-C$_6$), cycloalkyls (C$_3$-C$_8$), heterocycloalkyls containing one or more of O, S, and N, optional substituted aryls, or optionally substituted heteroaryls, R$^9$, R$^{10}$, R$^{11}$, R$^{12}$, R$^{13}$=H, alkyls (C$_1$-C$_6$), cycloalkyls (C$_3$-C$_8$), heterocycloalkyls containing one or more of O, S, and N, optionally substituted aryls, or optionally substituted heteroaryls, R$^2$ is selected from a group consisting of H, OH, NH$_2$, OR$^{14}$, NR$^{14}$R$^{15}$, alkyl, aryl, heteroaryl, cycloalkyl, arylalkyl, heterocyclyl, heterocyclylalkyl, alkenyl, and alkynyl, where R$^{14}$, and R$^{15}$ are selected from: H; alkyl (C$_1$-C$_8$); cycloalkyl (C$_3$-C$_8$) optionally substituted by a group selected from alkyls (C$_1$-C$_8$), cycloalkyls (C$_3$-C$_8$), aryls, and heteroaryls; —OR$^{17}$; —SR$^{17}$; —NR$^{17}$R$^{18}$; —S(O)R$^{17}$; —S(O)$_2$R$^{17}$; —S(O)$_2$NR$^{17}$R$^{18}$; —C(O)NR$^{17}$R$^{18}$; —N(R$^{17}$)C(O)R$^{18}$; —N(R$^{17}$)S(O)$_2$R$^{18}$; —N(R$^{17}$)C(O)N(R$^{18}$R$^{19}$); —N(R$^{17}$)C(O)OR$^{18}$; optionally substituted aryl; optionally substituted heteroaryl; optionally substituted aryalkyl; optionally substituted heterocyclyl; optionally substituted heterocyclyalkyl; optionally substituted alkenyl; and optionally substituted alkynyl;

where R$^{17}$, R$^{18}$ and R$^{19}$ are respectively chosen from H, alkyl (C$_1$-C$_8$), cycloalkyls (C$_3$-C$_8$), optionally substituted aryl, optionally substituted alkylaryl, and optionally substituted heteroaryl;

or R$^{14}$ and R$^{15}$ are part of a ring containing 0-3 heteroatoms selected from N, O, and S;

and

R$^3$ is selected from the group consisting of H, alkyl, aryl, heteroaryl, cycloalkyl, arylalkyl, heterocyclyl, heterocyclylalkyl, alkenyl, and alkynyl.

2. The method of claim 1, wherein the cancer is gastric cancer, or colon cancer.

3. The method of claim 1, wherein in the compound of Formula I,
X=CH;
Y=S;
W=N;
L=N;
R$^1$ is selected from following groups:

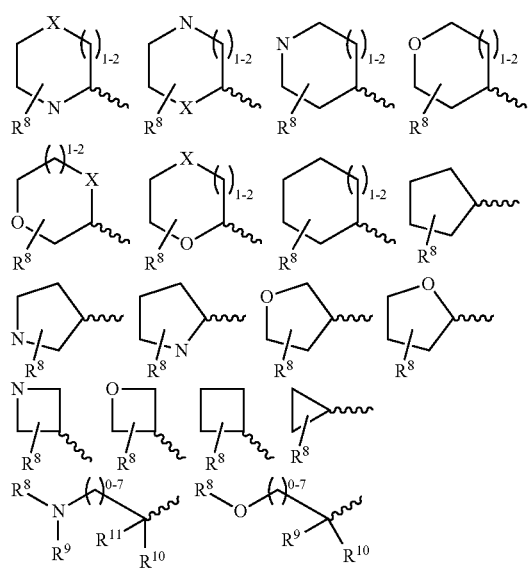

-continued

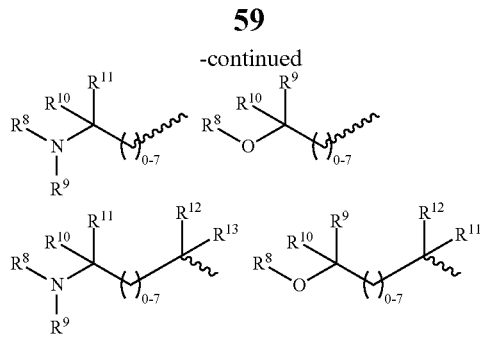

where X=CH$_2$, NH, S, or O;

R$^8$=—H, —NH$_2$, —OH, —N(R$^4$, R$^5$), —C(R$^4$R$^5$)$_{1-7}$NR$^6$R$^7$, —C(R$^4$R$^5$)$_{1-7}$OR$^6$, —N(R$^4$)NR$^5$R$^6$

R$^4$, R$^5$, R$^6$, R$^7$=H, alkyls (C$_1$-C$_6$), cycloalkyls (C$_3$-C$_8$), heterocycloalkyls containing one or more of O, S, and N, optional substituted aryls, or optionally substituted heteroaryls, R$^9$, R$^{10}$, R$^{11}$, R$^{12}$, R$^{13}$=H, alkyls (C$_1$-C$_6$), cycloalkyls (C$_3$-C$_8$), heterocycloalkyls containing one or more of O, S, and N, optionally substituted aryls, or optionally substituted heteroaryls, R$^2$ is selected from a group consisting of H, OH, NH$_2$, OR$^{114}$, NR$^{114}$R$^{115}$, alkyl, aryl, heteroaryl, cycloalkyl, arylalkyl, heterocyclyl, heterocyclylalkyl, alkenyl, and alkynyl, where R$^{114}$, and R$^{115}$ are selected from: H; alkyl (C$_1$-C$_8$); cycloalkyl (C$_3$-C$_8$) optionally substituted by a group selected from alkyls (C$_1$-C$_8$), cycloalkyls (C$_3$-C$_8$), aryls, and heteroaryls; —OR$^{17}$; —SR$^{17}$; —NR$^{17}$R$^{18}$; —S(O)R$^{17}$; —S(O)$_2$R$^{17}$; —S(O)$_2$NR$^{17}$R$^{18}$; —C(O)NR$^{17}$R$^{18}$; —N(R$^{17}$)C(O)R$^{18}$; —N(R$^{17}$)S(O)$_2$R$^{18}$; —N(R$^{17}$)C(O)N(R$^{18}$R$^{19}$); —N(R$^{17}$)C(O)OR$^{18}$; optionally substituted aryl; optionally substituted heteroaryl; optionally substituted aryalkyl; optionally substituted heterocyclyl; optionally substituted heterocyclyalkyl; optionally substituted alkenyl; and optionally substituted alkynyl;

where R$^{17}$, R$^{18}$ and R$^{19}$ are respectively chosen from H, alkyl (C$_1$-C$_8$), cycloalkyls (C$_3$-C$_8$), optionally substituted aryl, optionally substituted alkylaryl, and optionally substituted heteroaryl;

or R$^{114}$, and R$^{115}$ are part of a ring containing 0-3 heteroatoms selected from N, O, and S;

and

R$^3$ is selected from the group consisting of H, alkyl, aryl, heteroaryl, cycloalkyl, arylalkyl, heterocyclyl, heterocyclylalkyl, alkenyl, and alkynyl.

4. The method of claim 3, wherein R$^3$ is selected from the following groups:

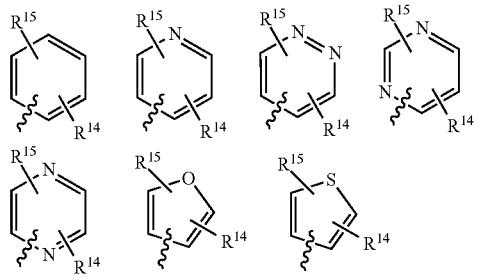

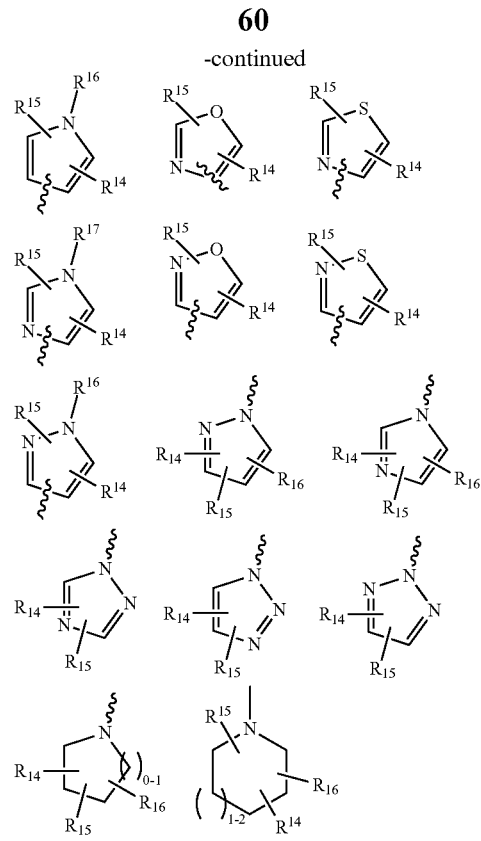

where R$^{14}$, R$^{15}$ and R$^{16}$ are selected from following groups: H; alkyl (C$_1$-C$_8$); cycloalkyl (C$_3$-C$_8$) optionally substituted with alkyls (C$_1$-C$_8$), cycloalkyls (C$_3$-C$_8$), aryls, heteroaryls; —OR$^{17}$; —SR$^{17}$; —NR$^{17}$R$^{18}$; —S(O)R$^{17}$; —S(O)2R$^{17}$; —S(O)2NR$^{17}$R$^{18}$; —C(O)NR$^{17}$R$^{18}$; —N(R$^{17}$)C(O)R$^{18}$; —N(R$^{17}$)S(O)$_2$R$^{18}$; —N(R$^{17}$)C(O)N(R$^{18}$R$^{19}$); —N(R$^{17}$)C(O)OR$^{18}$; optionally substituted aryl; optionally substituted heteroaryl; optionally substituted aryalkyl; optionally substituted heterocyclyl; optionally substituted heterocyclyalkyl; optionally substituted alkenyl; and optionally substituted alkynyl;

where R$^{17}$, R$^{18}$ and R$^{19}$ are respectively chosen from H, alkyl (C$_1$-C$_8$), cycloalkyls (C$_3$-C$_8$), optionally substituted aryl, optionally substituted alkylaryl, and optionally substituted heteroaryl;

or R$^{14}$, R$^{15}$ and R$^{16}$ can be part of ring containing 0-3 heteroatoms selected from N, O, and S.

5. The method of claim 3, wherein R$^2$ is selected from the following groups:

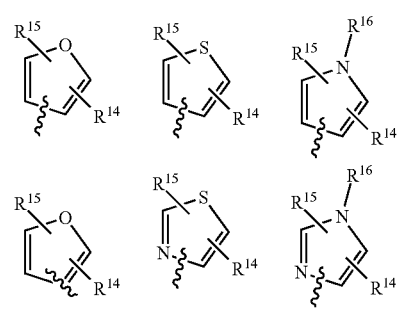

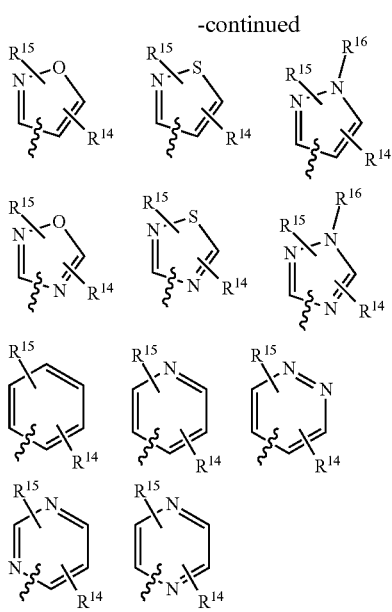

wherein R$^{14}$, R$^{15}$, R$^{16}$=H; alkyl (C$_1$-C$_8$); cycloalkyl (C$_3$-C$_8$) optionally substituted with a group selected from alkyls (C$_1$-C$_8$), cycloalkyls (C$_3$-C$_8$), aryls, and heteroaryls; —OR$^{17}$; —SR$^{17}$; —NR$^{17}$R$^{18}$; —S(O)R$^{17}$; —S(O)2R$^{17}$: —S(O)2NR$^{17}$R$^{18}$; —C(O)NR$^{17}$R$^{18}$; —N(R$^{17}$)C(O)R$^{18}$; —N(R$^{17}$)S(O)$_2$R$^{18}$; —N(R$^{17}$)C(O)N(R$^{18}$R$^{19}$); —N(R$^{17}$)C(O)OR$^{18}$; optionally substituted aryl; optionally substituted heteroaryl; optionally substituted aryalkyl; optionally substituted heterocyclyl; optionally substituted heterocyclyalkyl; optionally substituted alkenyl; and optionally substituted alkynyl;

where R$^{17}$ and R$^{18}$ are respectively chosen from H, alkyl (C$_1$-C$_8$), cycloalkyls (C$_3$-C$_8$), optionally substituted aryl, optionally substituted alkylaryl, and optionally substituted heteroaryl;

or, R$^{14}$, R$^{15}$ and R$^{16}$ are part of ring containing 0-3 heteroatoms selected from N, O, and S.

6. A method for treating a cancer that can be treated by inhibition of checkpoint protein kinases CHK1 or CHK2, wherein the cancer is selected from the group consisting of gastric cancer, colon cancer, lung cancer, ovarian cancer, and sarcoma, comprising administering to a patient in need thereof a therapeutically effective amount of a pharmaceutical composition comprising a pharmaceutically acceptable excipient and a therapeutically effective amount of a compound of formula II:

(II)

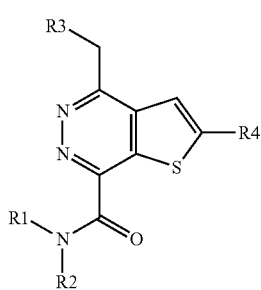

wherein R$^1$ and R$^2$ are independently H or C$_{1-4}$ alkyl; R$^3$ is a saturated or unsaturated 5- or 6-membered heterocyclic ring containing at least one N, S, or O, or a stereoisomer thereof; and R$^4$ is a phenyl substituted by one or two halogen atoms.

7. The method of claim 6, wherein R$^1$=R$^2$=H.

8. The method of claim 6, wherein R$^3$ is a saturated 6-membered heterocyclic ring containing at least one N, or O, or a stereoisomer thereof.

9. The method of claim 8, wherein R$^3$ is hexahydropyridinyl, tetrahydropyranyl, tetrahydrothiopyranyl, tetrahdropyrrolidinyl, tetrahydropyrolyl, tetrahydrofuranyl, or tetrahydro-thiophenyl, or a stereoisomer thereof.

10. The new of claim 9, wherein R$^3$ is hexahydropyridinyl.

11. The method of claim 6, wherein R$^4$ is a phenyl substituted once with a halogen atom.

12. The method of claim 6, wherein R$^4$ is

wherein X is F, Cl, Br, or I.

13. The method of claim 6, wherein the compound is selected from the group consisting of:

1

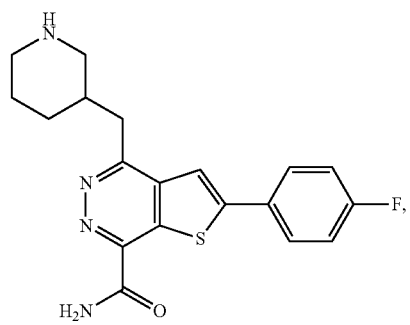

2

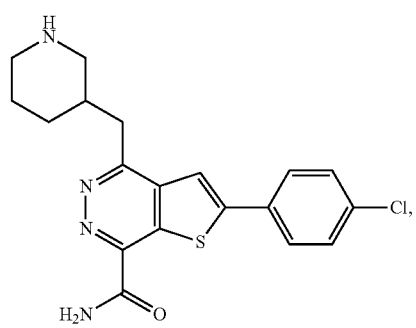

3

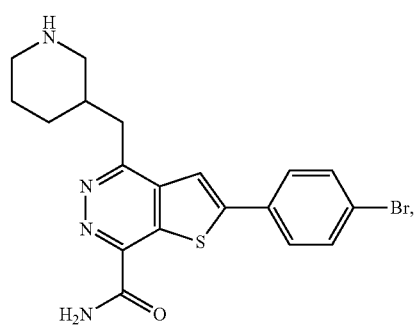

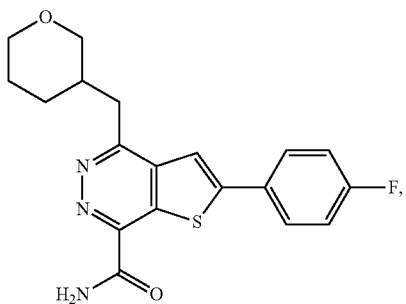
4
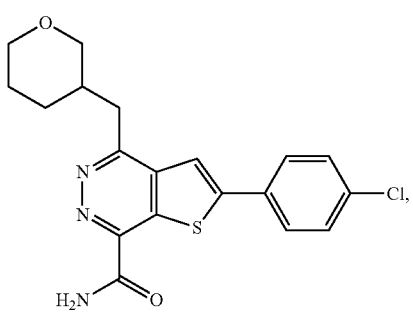
5
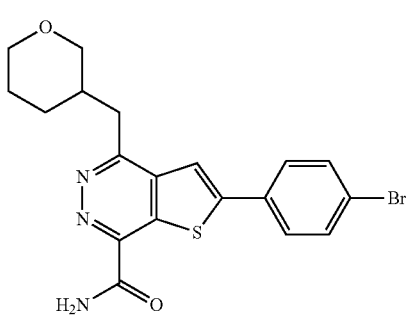
6
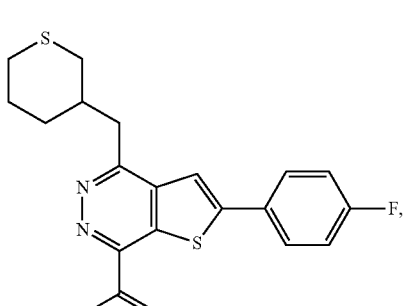
7
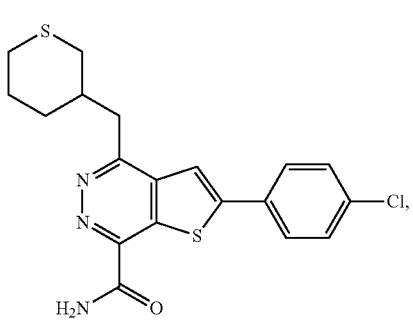
8
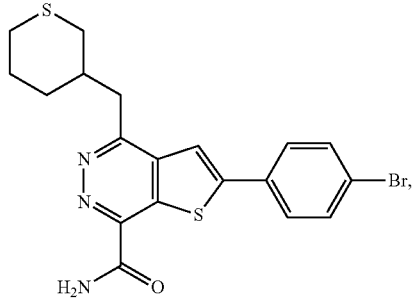
9
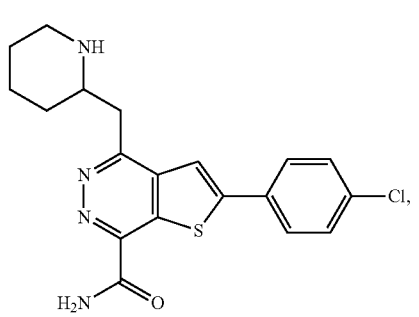
10
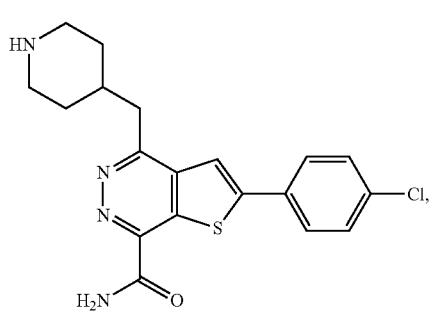
11
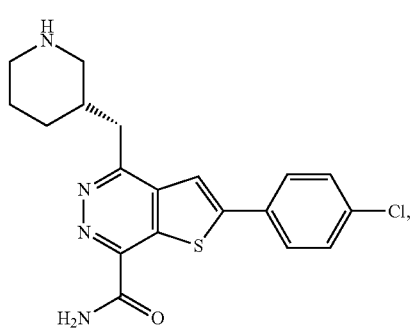
12
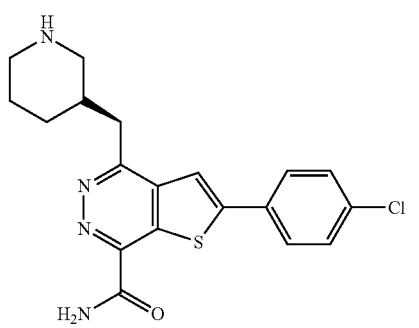
13

14
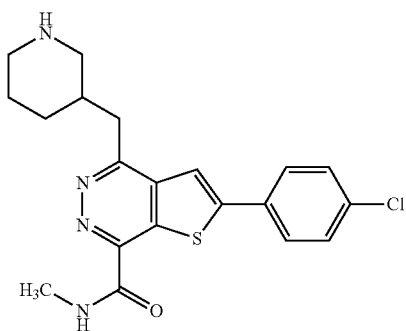
15
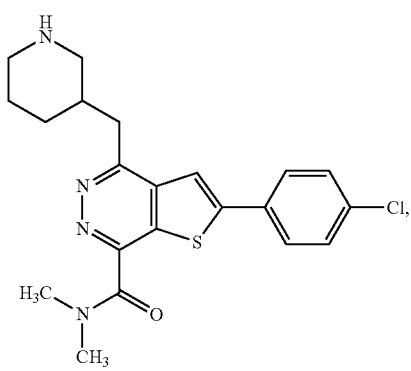
16
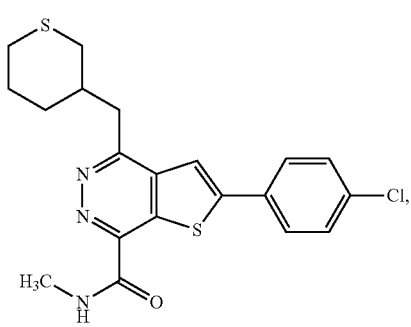
17
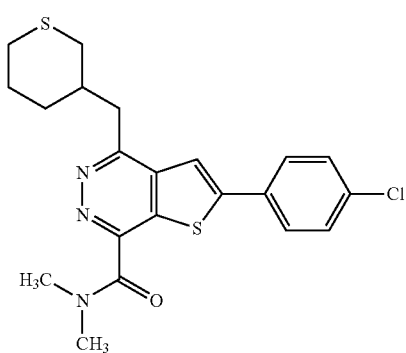
18
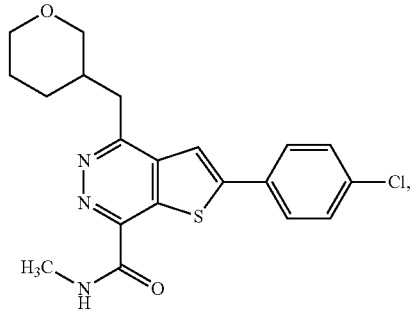
19
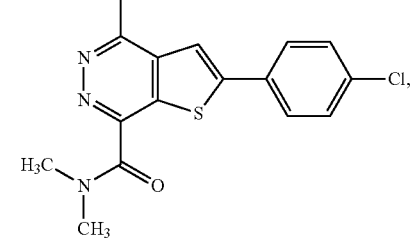
20
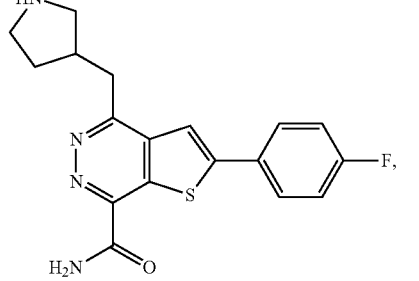
21
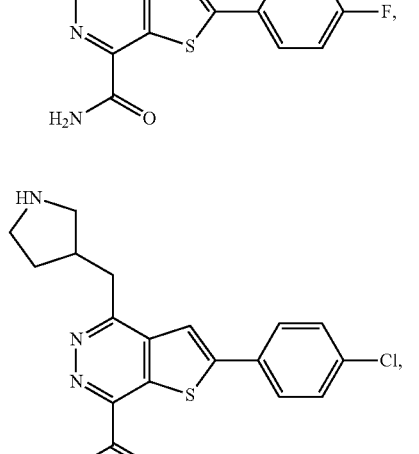
22
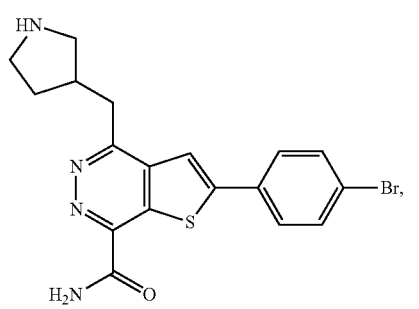

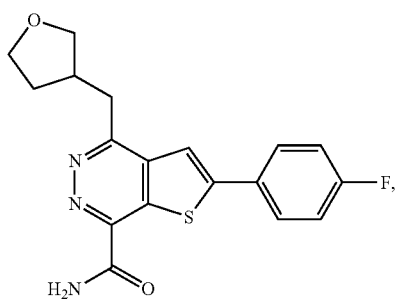 23
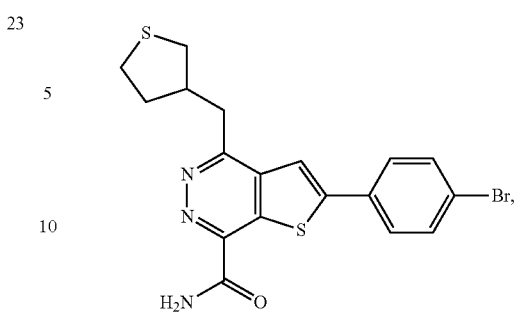 28
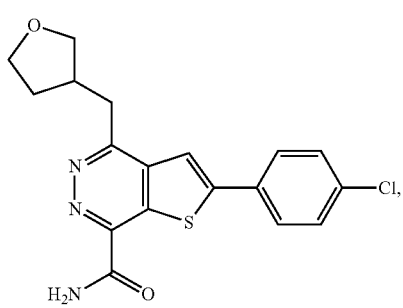 24
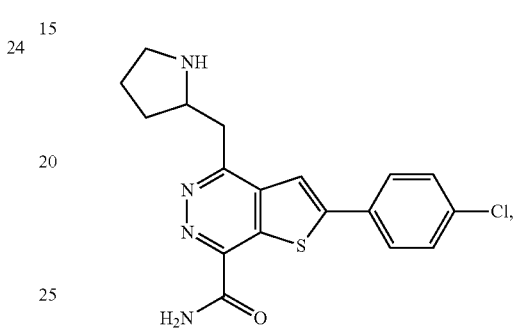 29
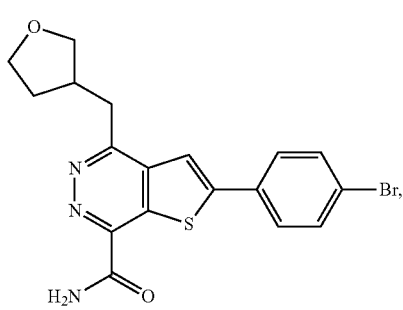 25
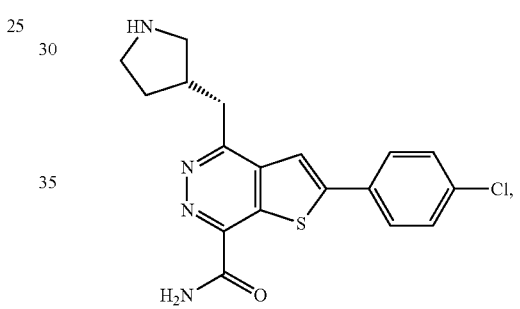 30
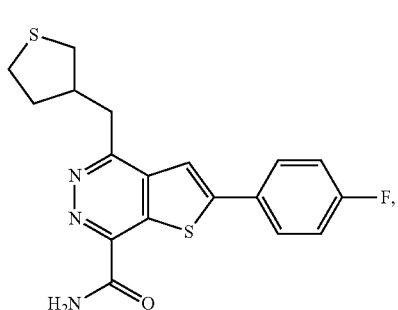 26
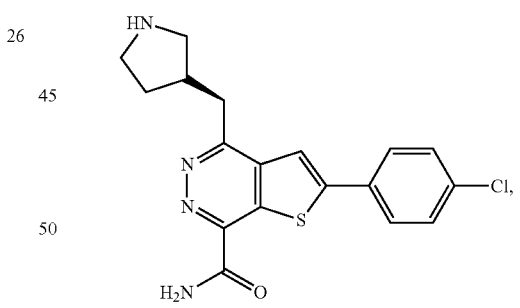 31
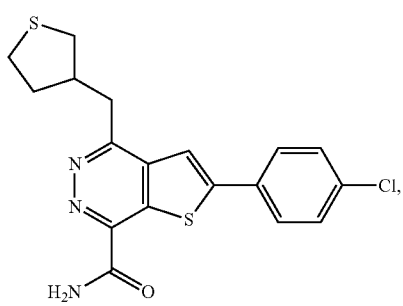 27
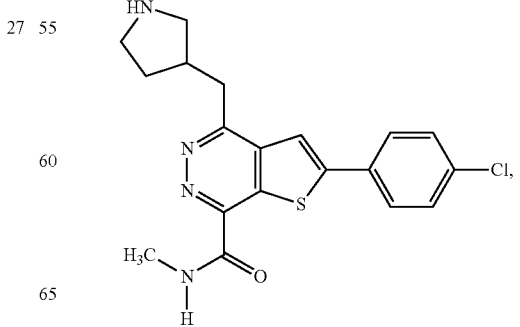 32

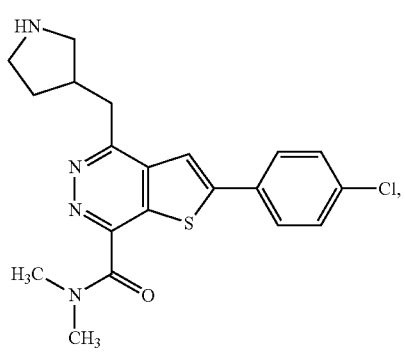
33
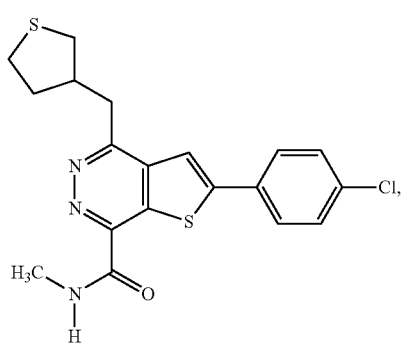
34
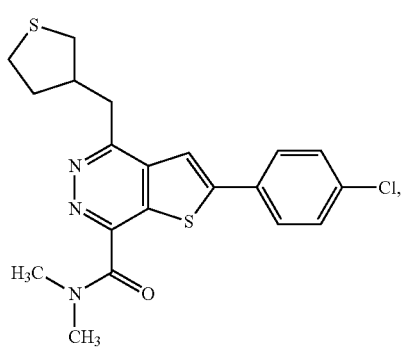
35
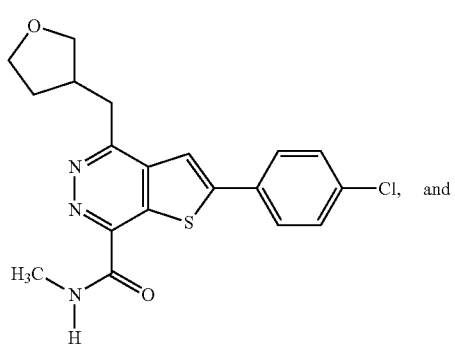
36
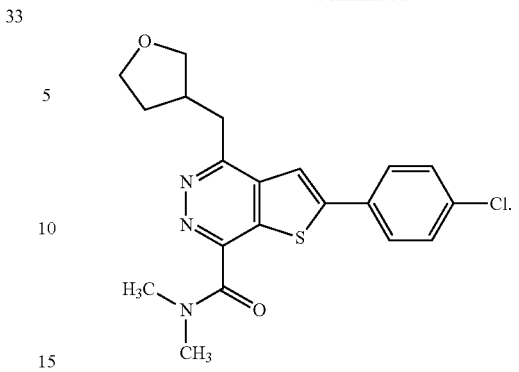
37
14. The method of claim 6, wherein $R^3$ is pyridinyl, α- or γ-pyranyl, α-thiapyranyl, γ-thiapyranyl, pyrolyl, furanyl, or thiophenyl, or a stereoisomer thereof.
15. The method of claim 6, wherein the compound is:
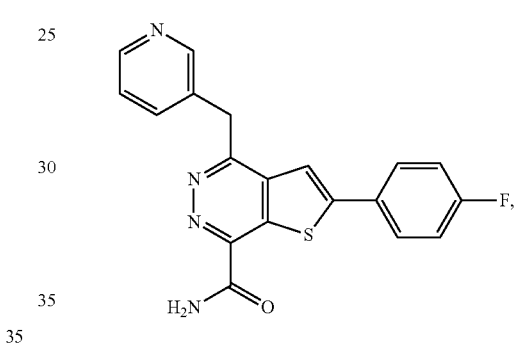
38
39
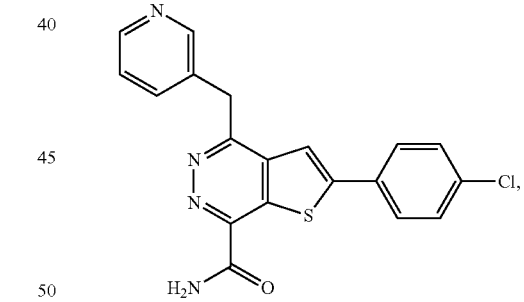
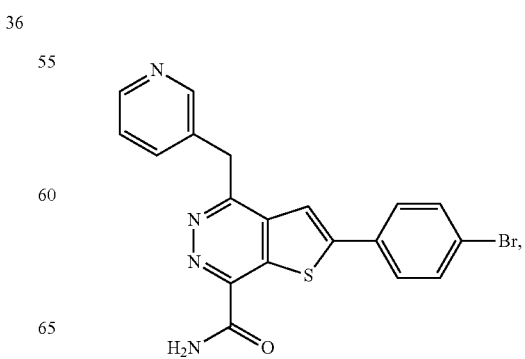
40

| 41A | 43B |
|---|---|
| 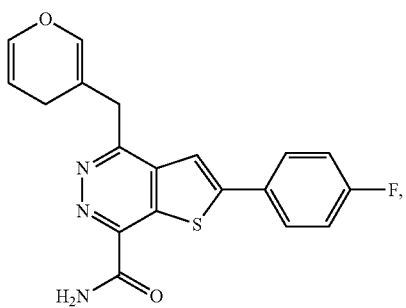 | 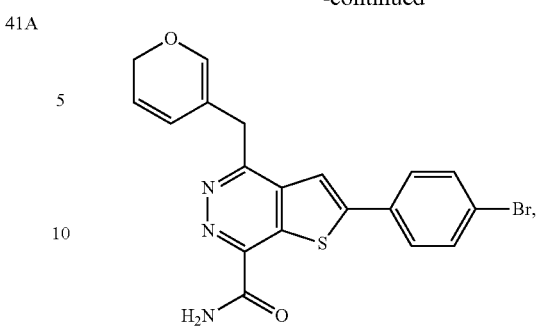 |
| 41B | 44A |
| 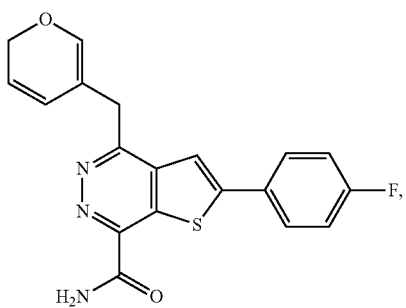 | 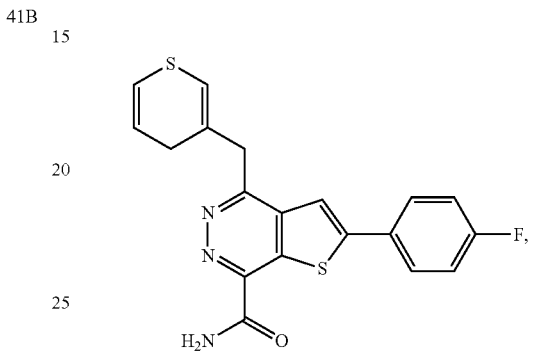 |
| 42A | 44B |
| 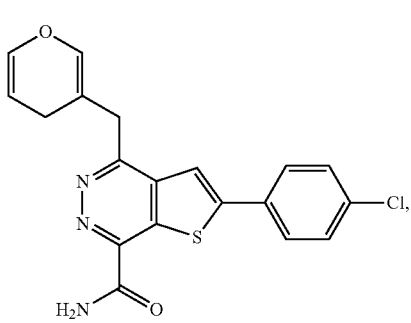 | 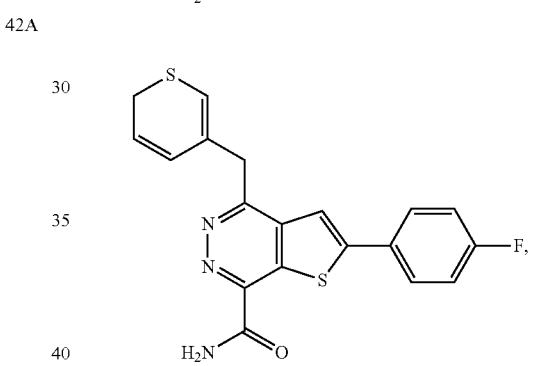 |
| 42B | 45A |
| 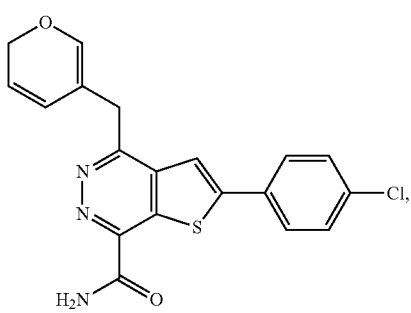 | 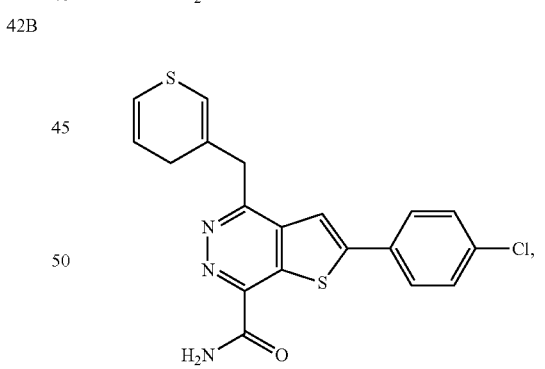 |
| 43A | 45B |
| 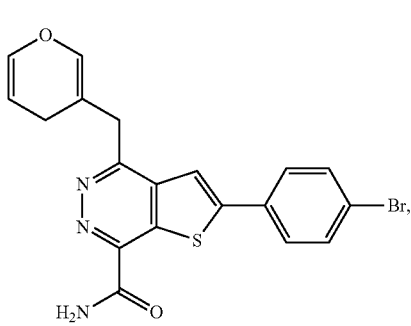 | 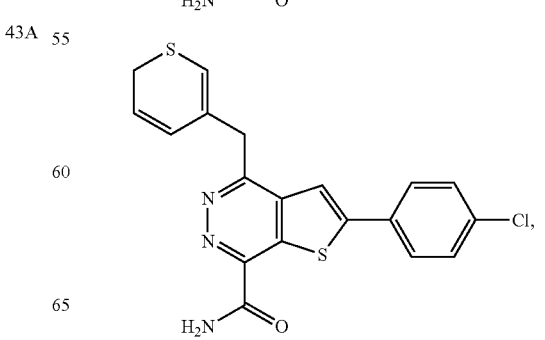 |

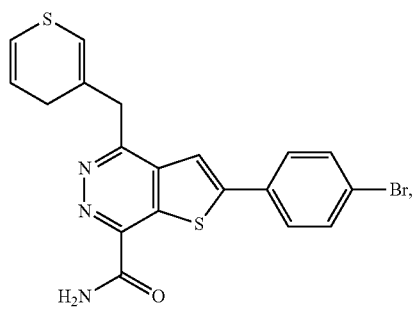
46A
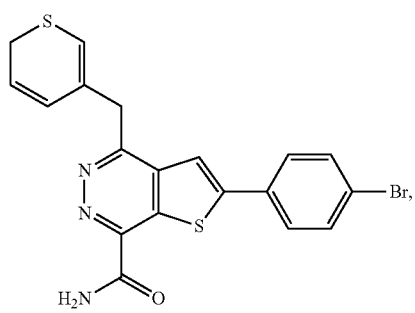
46B
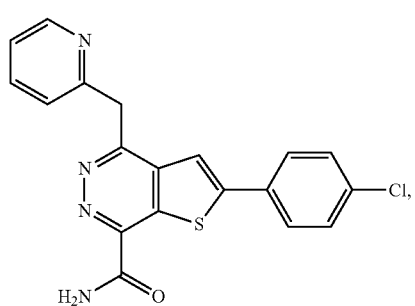
47
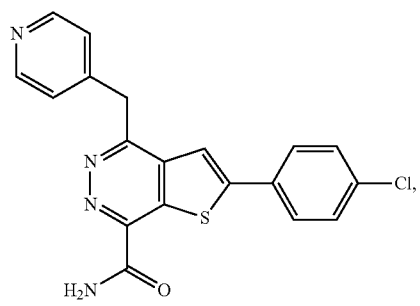
48
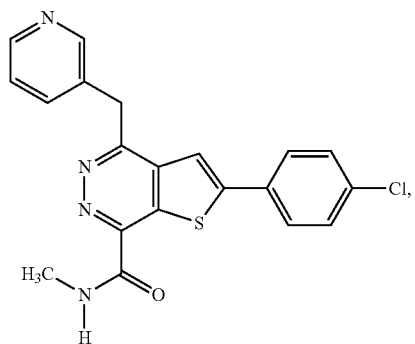
49
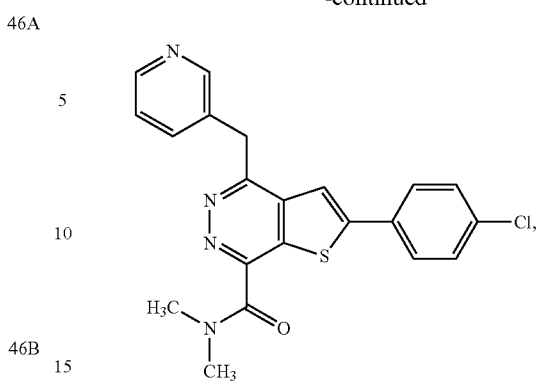
50
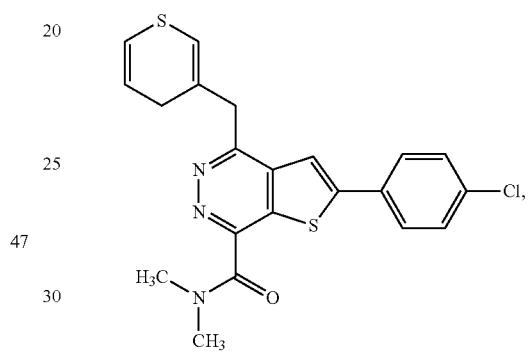
51A
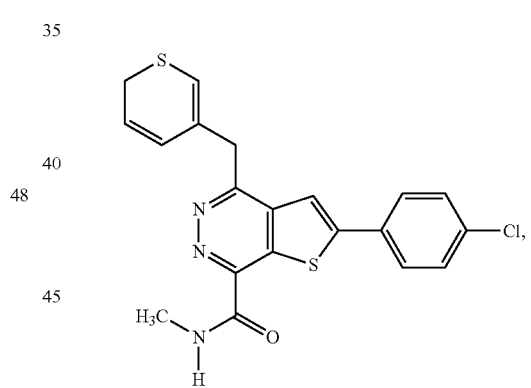
51B
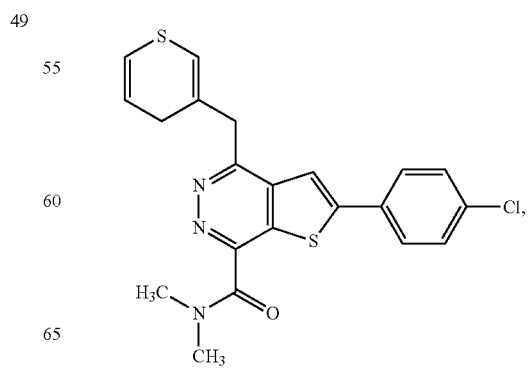
52A 75
-continued
52B
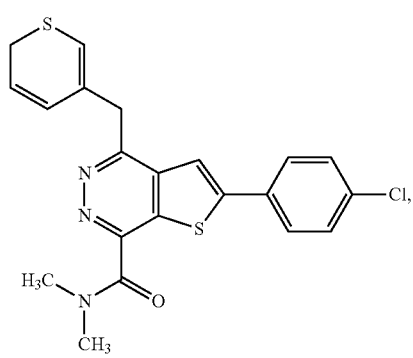
53A
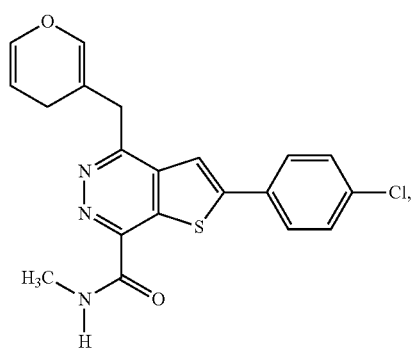
53B
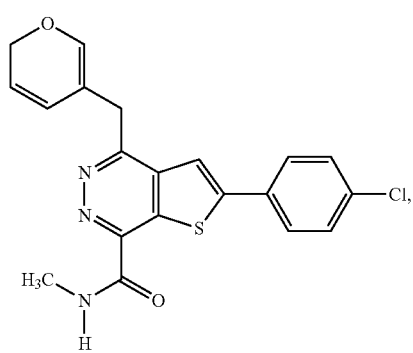
54A
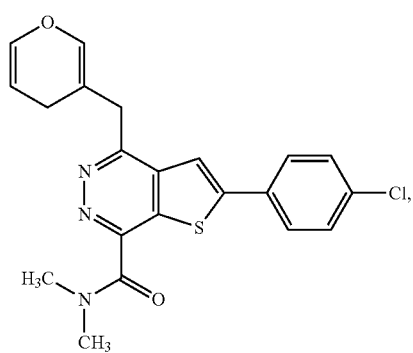
76
-continued
54B
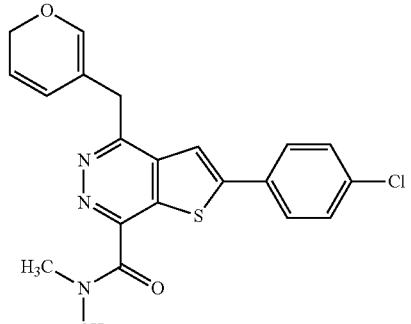
55
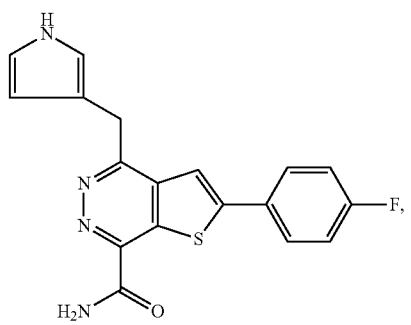
56
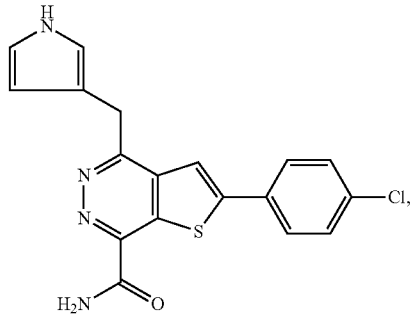
57
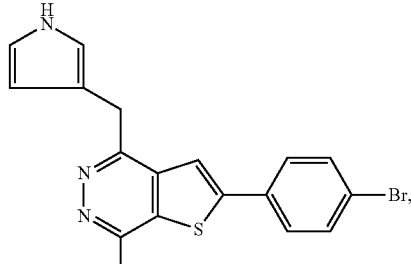
58
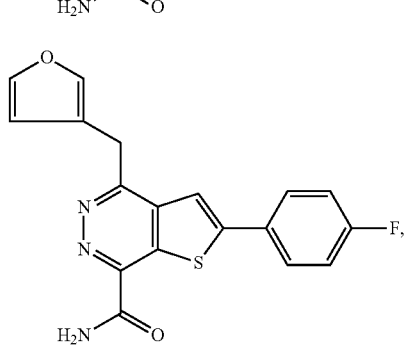

77
-continued
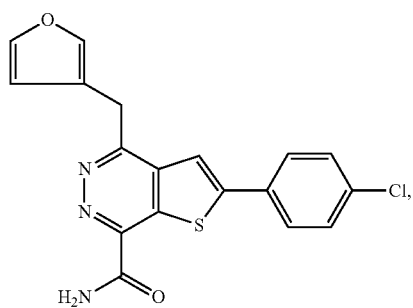
59
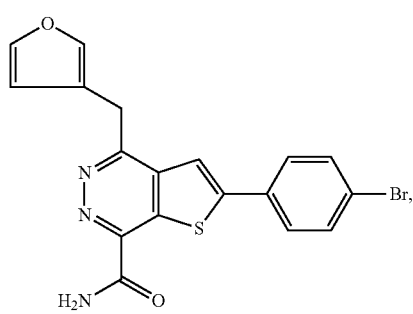
60
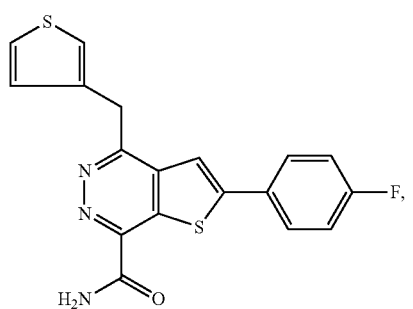
61
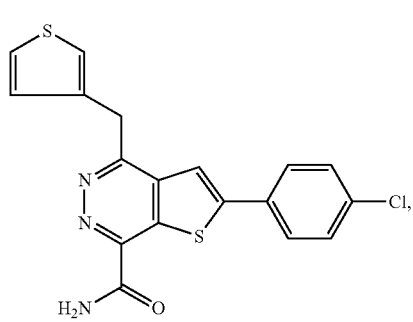
62
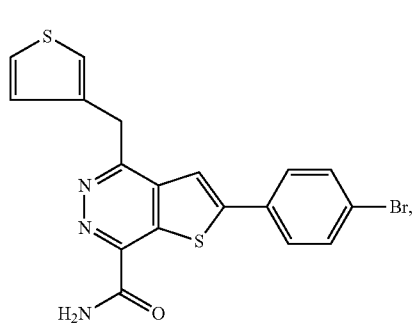
63
78
-continued
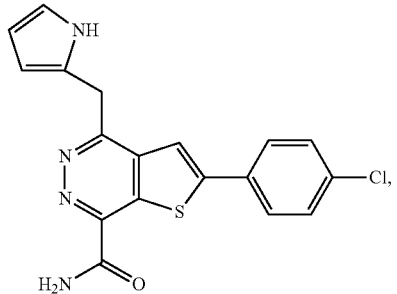
64
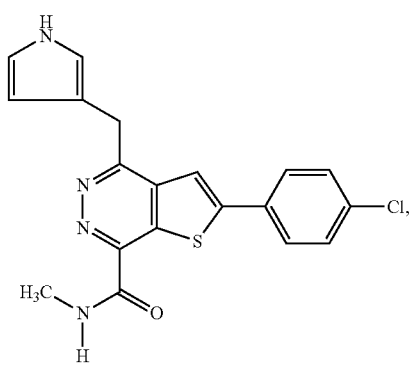
65
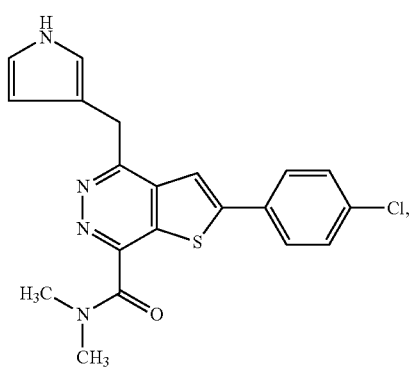
66
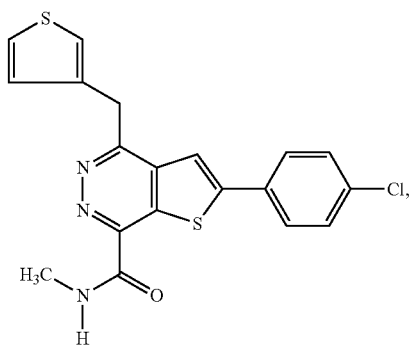
67

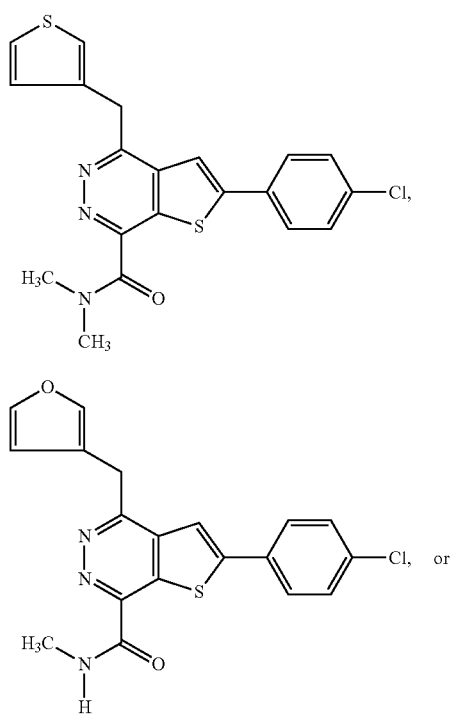
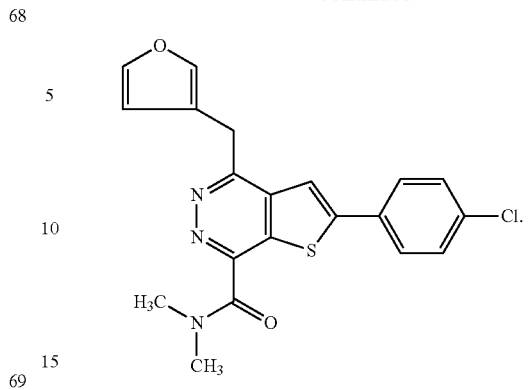
16. The method of claim 1, further comprising administering to the patient an anticancer agent selected from the group consisting of Gemcitabine, Adriamycin and irinotecan.
17. The method of claim 6, further comprising administering to the patient an anticancer agent selected from the group consisting of Gemcitabine, Adriamycin and irinotecan.
* * * * *